United States Patent
Deliencourt-Godefroy et al.

(10) Patent No.: US 10,351,501 B2
(45) Date of Patent: Jul. 16, 2019

(54) GEM DIFLUOROCOMPOUNDS AS DEPIGMENTING OR LIGHTENING AGENTS

(71) Applicant: TFCHEM, Val de Reuil (FR)

(72) Inventors: Géraldine Deliencourt-Godefroy, Bois D'ennebourg (FR); Lénaïg Lopes, Le Petit Quevilly (FR)

(73) Assignee: TFCHEM, Val de Reuil (FR)

( * ) Notice: Subject to any disclaimer, the term of this patent is extended or adjusted under 35 U.S.C. 154(b) by 0 days.

(21) Appl. No.: 15/551,686

(22) PCT Filed: Mar. 4, 2016

(86) PCT No.: PCT/EP2016/054623
§ 371 (c)(1),
(2) Date: Aug. 17, 2017

(87) PCT Pub. No.: WO2016/139336
PCT Pub. Date: Sep. 9, 2016

(65) Prior Publication Data
US 2018/0029967 A1    Feb. 1, 2018

(30) Foreign Application Priority Data

Mar. 4, 2015    (WO) .................. PCT/IB2015/000510

(51) Int. Cl.
| | |
|---|---|
| *C07C 43/247* | (2006.01) |
| *A61K 8/69* | (2006.01) |
| *A61Q 19/02* | (2006.01) |
| *C07C 69/63* | (2006.01) |
| *C07C 43/253* | (2006.01) |
| *C07C 43/315* | (2006.01) |
| *C07C 49/753* | (2006.01) |
| *C07D 317/72* | (2006.01) |
| *A61K 8/33* | (2006.01) |
| *A61K 8/34* | (2006.01) |
| *A61K 8/35* | (2006.01) |
| *A61K 8/37* | (2006.01) |
| *A61K 8/49* | (2006.01) |
| *C07C 53/08* | (2006.01) |

(52) U.S. Cl.
CPC .............. *C07C 43/247* (2013.01); *A61K 8/33* (2013.01); *A61K 8/347* (2013.01); *A61K 8/35* (2013.01); *A61K 8/37* (2013.01); *A61K 8/4973* (2013.01); *A61K 8/69* (2013.01); *A61Q 19/02* (2013.01); *C07C 43/253* (2013.01); *C07C 43/315* (2013.01); *C07C 49/753* (2013.01); *C07C 53/08* (2013.01); *C07C 69/63* (2013.01); *C07D 317/72* (2013.01); *C07C 2601/14* (2017.05)

(58) Field of Classification Search
CPC .................................................. C07C 43/247
USPC ....................................................... 549/336
See application file for complete search history.

(56) References Cited

FOREIGN PATENT DOCUMENTS

| | | |
|---|---|---|
| WO | WO-2012/160218 A1 | 11/2012 |
| WO | WO-2013/103874 A1 | 7/2013 |

OTHER PUBLICATIONS

"Vingt-quaterime directive 2006/6/Ce de la commission", Official J. Eur. Commun., 2000, L56, pp. 42-46.
Bang et al., "Hydrolysis of arbutin to hydroquinone by human skin bacteria and its effect on antioxidant activity", Journal of Cosmetic Dermatology, 2008, vol. 7, pp. 189-193.
Coiffard et al., "Degradation kinetics of arbutin in solution", Pharm. Ind., 1999, vol. 61, pp. 574-576.
Ebanks et al., "Mechanisms regulating skin pigmentation: the rise and fall of complexion coloration", Int. J. Mol. Sci., 2009, vol. 10, pp. 4066-4087.
Kanthraj, "Skin-lightening agents: new chemical and plant extracts—ongoing search for the Holy Grail", Indian J. Dermatol Venereol Leprol, 2010, vol. 76, pp. 3-6.
Popovici et al., "Evaluation de l'activite antioxidant des composes phenoliques par la reactivite avec le radical libre DPPH", Revue de genie industriel, 2009, vol. 4, pp. 25-39.
Sunnemann et al., "Stille-heck coupling sequences applied in a versatile new access to steroid skeletons", Chem. Eur. J., 2007, vol. 13, pp. 3739-3756.
Yang et al., "Comparative study on the photostability of arbutin and deoxy arbutin: sensitivity to ultraviolet radiation and enhanced photostability by the water-soluble sunscreen, Benzophenone-4", Biosci. Biotechnol. Biochem, 2013, vol. 77, No. 5, pp. 1127-1130.
Boissy et al., "DeoxyArbutin: a novel reversible tyrosinase inhibitor with effective in vivo skin lightening potency", Experimental Dermatology, 2005, vol. 14, pp. 601-608.
International Search Report issued in International Patent Application No. PCT/EP2016/054623, dated Apr. 19, 2016.

*Primary Examiner* — Taofiq A Solola
(74) *Attorney, Agent, or Firm* — Sunit Talapatra; Foley & Lardner LLP

(57) ABSTRACT

The present invention relates to a compound having the formula (I), as well as a method for preparing such a compound, a cosmetic or pharmaceutic composition containing such a compound, and the use thereof as a depigmenting, lightening, bleaching or whitening agent and for treating pigmentation disorders, notably by topical application on the skin.

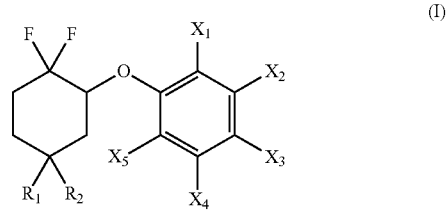

13 Claims, 1 Drawing Sheet

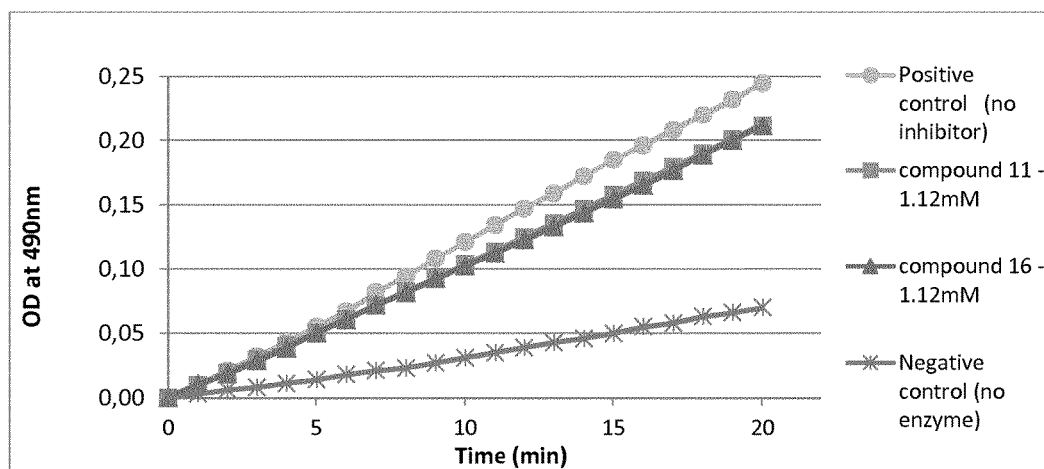

GEM DIFLUOROCOMPOUNDS AS DEPIGMENTING OR LIGHTENING AGENTS

CROSS-REFERENCE TO RELATED APPLICATIONS

This application is the National Phase of International Patent Application No. PCT/EP2016/054623, filed Mar. 4, 2016, published on Sep. 9, 2016 as WO 2016/139336 A1, which claims priority to International Patent Application No. PCT/IB2015/000510, filed Mar. 4, 2015. The contents of these applications are herein incorporated by reference in their entirety.

The present invention relates to a new family of gem difluorocompounds, their preparation processes, the cosmetic and pharmaceutical compositions containing such compounds, as well as their use for cosmetic and pharmaceutical applications, in particular as depigmenting, lightening, bleaching or whitening agents and for treating pigmentation disorders such as hyperpigmentation.

Since several years, people try to lighten their skin in particular in Asia and Africa. Melanin present in melanocytes and produced by catalyze transformation of tyrosine by the enzyme tyrosinase, is the pigment responsible for skin coloration. An over-production of melanin causes an hyperpigmentation of the skin due to for examples an excessive sun exposition (*lentigo solaris*, ephelides), hormone disorder (melasma, chloasma), diseases, medication, chemicals, drugs, injuries or scars (acne, burns, cuts) or age spots (*lentigo senilis*).

The most popular ingredients for skin lightening, skin bleaching or skin whitening are, hydroquinone, arbutin (alpha and beta), kojic acid, licorice extract, niacinamide (B3 vitamin) and many others (*Int. J. Mol. Sci.* 2009, 10, 4066-4087).

Hydroquinone has been one of the first and most efficient depigmenting agents. Although its efficacy has been proven, in the start of the 21$^{st}$ century, hydroquinone began to be removed or its uses to be limited in cosmetics due to its potential dermatological and systemic side effects (*Official J. Eur. Commun.* 2000, L56, 42-46; *Indian J. Dermatol. Venereol. Leprol.* 2010, 76, 3-6).

Arbutin (natural product extracted from plants) is a glycosylated derivative of hydroquinone and an efficient tyrosinase inhibitor more stable and less toxic than hydroquinone. However, despite its huge potential, alpha and beta arbutin remain unstable, and undergo hydrolysis under different conditions which leads to the release of hydroquinone.

Other derivatives have been built in order to increase skin absorption and efficiency. It is the case of deoxyarbutin. However, such compound still contains an acetal function which is susceptible to hydrolysis and concomitant release of hydroquinone (*J. Cosmet. Dermatol.* 2008, 7, 189-193; *Pharm. Ind.* 1999, 61, 574-576; *Biosci. Biotechnol. Biochem.* 2013, 77, 1127-1130).

As a result there is a need for new inhibitors of tyrosinase activity with safer profile, more stable, more efficient, with improved skin absorption, and with short synthetic access.

Thus, the inventors have developed a new family of gem difluorocompounds useful as tyrosinase inhibitors, in particular for cosmetic or pharmaceutical applications and more particularly as depigmenting, lightening, bleaching or whitening agents and for treating pigmentation disorders such as hyperpigmentation.

Thereby, the present invention relates to a compound having the following formula (I):

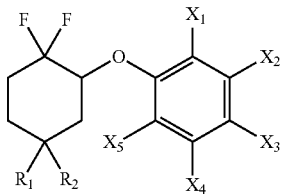

or a cosmetically or a pharmaceutically acceptable salt thereof, a stereoisomer or a mixture of stereoisomers in any proportion, particularly an enantiomer or a mixture of enantiomers, and more particularly a racemate mixture, wherein:

$R_1$ and $R_2$ represent, independently from each other, a hydrogen atom, $OSiR_3R_4R_5$, $OR_6$, $OC(O)R_7$, $OCO_2R_8$, $OC(O)NR_9R_{10}$, $OP(O)(OR_{11})_2$, or $OSO_3R_{12}$, or $R_1$ and $R_2$ form together an oxo group (=O), or $R_1$ and $R_2$ are linked together by a chain of formula —O(CH$_2$)$_n$O—, with n representing 2 or 3, and advantageously 2, and $X_1$, $X_2$, $X_3$, $X_4$, $X_5$ represent, independently from one another, a hydrogen atom, $OSiR_{13}R_{14}R_{15}$, $OR_{16}$, $OC(O)R_{17}$, $OCO_2R_{18}$, $OC(O)NR_{19}R_{20}$, $OP(O)(OR_{21})_2$, or $OSO_3R_{22}$, with:

$R_3$, $R_4$, $R_5$, $R_{13}$, $R_{14}$ and $R_{15}$ representing, independently from one another, a $(C_1-C_6)$alkyl, aryl, aryl-$(C_1-C_6)$alkyl or $(C_1-C_6)$alkyl-aryl group, $R_6$ and $R_{16}$ representing, independently from one another, a hydrogen atom; a O-protecting group; or a $(C_1-C_6)$alkyl, $(C_2-C_6)$alkenyl, $(C_2-C_6)$alkynyl, $(C_3-C_7)$cycloalkyl, 5- to 7-membered heterocycloalkyl, aryl, heteroaryl, $(C_3-C_7)$cycloalkyl-$(C_1-C_6)$alkyl, (5- to 7-membered heterocycloalkyl)-$(C_1-C_6)$alkyl, aryl-$(C_1-C_6)$alkyl or heteroaryl-$(C_1-C_6)$alkyl group, said group being optionally substituted by one or several groups selected from a halogen atom, a $(C_1-C_6)$alkyl group and a $(C_1-C_6)$alkoxy group, $R_7$, $R_8$, $R_{17}$ and $R_{18}$ representing, independently from one another, a $(C_1-C_6)$alkyl, $(C_2-C_6)$alkenyl, $(C_2-C_6)$alkynyl, $(C_3-C_7)$cycloalkyl, 5- to 7-membered heterocycloalkyl, aryl, heteroaryl, $(C_3-C_7)$cycloalkyl-$(C_1-C_6)$alkyl, (5- to 7-membered heterocycloalkyl)-$(C_1-C_6)$alkyl, aryl-$(C_1-C_6)$alkyl or heteroaryl-$(C_1-C_6)$alkyl group, said group being optionally substituted by one or several groups selected from a halogen atom, a $(C_1-C_6)$alkyl group and a $(C_1-C_6)$alkoxy group, $R_9$, $R_{10}$, $R_{19}$ and $R_{20}$ representing, independently from one another, a hydrogen atom; a N-protecting group; or a $(C_1-C_6)$alkyl, $(C_2-C_6)$alkenyl, $(C_2-C_6)$alkynyl, $(C_3-C_7)$cycloalkyl, 5- to 7-membered heterocycloalkyl, aryl, heteroaryl, $(C_3-C_7)$cycloalkyl-$(C_1-C_6)$alkyl, (5- to 7-membered heterocycloalkyl)-$(C_1-C_6)$alkyl, aryl-$(C_1-C_6)$alkyl or heteroaryl-$(C_1-C_6)$alkyl group, said group being optionally substituted by one or several groups selected from a halogen atom, a $(C_1-C_6)$alkyl group and a $(C_1-C_6)$alkoxy group, $R_{11}$, $R_{12}$, $R_{21}$ and $R_{22}$ representing, independently from one another, a hydrogen atom or a $(C_1-C_6)$alkyl group.

For the purpose of the present invention, "cosmetically or pharmaceutically acceptable" refers to what is useful in the preparation of a cosmetic or pharmaceutical composition, which is generally non-toxic, safe and acceptable for pharmaceutical and cosmetic use.

As used herein, "a cosmetically or pharmaceutically acceptable salt" is a salt which is cosmetically or pharmaceutically acceptable as defined herein, and which possesses the pharmaceutical and cosmetic properties and activity of the original compound. Such salt can be:

(1) acid addition salts formed with inorganic acids such as hydrochloric acid, bromhydric acid, sulphuric acid, nitric acid, phosphoric acid or the like; or formed with organic acids such as acetic acid, benzenesulfonic acid, benzoic acid, camphorsulfonic acid, citric acid, ethanesulfonic acid, fumaric acid, glucoheptonic acid, gluconic acid, glutamic acid, glycolic acid, hydroxynaphtoic acid, 2-hydroxyethanesulfonic acid, lactic acid, maleic acid, malic acid, mandelic acid, methanesulfonic acid, muconic acid, 2-naphtalenesulfonic acid, propionic acid, salicylic acid, succinic acid, dibenzoyl-L-tartaric acid, tartaric acid, p-toluenesulfonic acid, trimethylacetic acid, trifluoroacetic acid and the like, and (2) salts formed when an acid proton present in the parent compound is either replaced by a metal ion, e.g., an alkali metal ion (e.g., $Na^+$, $K^+$ or $Li^+$), an alkaline-earth metal ion (like $Ca^{2+}$ or $Mg^{2+}$) or an aluminium ion; or coordinates with an organic or inorganic base. Acceptable organic bases include diethanolamine, ethanolamine, N-methylglucamine, triethanolamine, tromethamine and the like. Acceptable inorganic bases include aluminium hydroxide, calcium hydroxide, potassium hydroxide, sodium carbonate and sodium hydroxide.

The term "stereoisomers" used in this invention refers to configurational stereoisomers, which include geometric isomers and optical isomers, and conformational isomers.

The geometric isomers, also called E/Z isomers or cis-trans isomers, result from the different position of substituents on a double C=C bond which can have a Z or E configuration, also called cis or trans configuration.

The optical isomers result from the different position in space of substituents or lone pair of electrons on an atom (such as a carbon or sulphur atom) comprising four different substituents (including potentially a lone pair of electron). This atom thus represents a chiral or asymmetric center. Optical isomers which are not mirror images of one another are thus designated as "diastereoisomers," and optical isomers which are non-superimposable mirror images are designated as "enantiomers".

The conformational isomers can be interconverted exclusively by rotations around one or several single bonds. In the case of the compounds of the present invention, the cyclohexane moiety can adopt a chair or boat conformation for example.

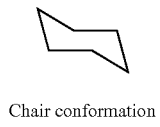   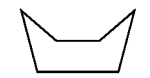

Chair conformation     Boat conformation

An equimolar mixture of two enantiomers of a chiral compound is designated as racemate mixture.

The term "$(C_1-C_6)$alkyl", as used in the present invention, refers to a straight or branched saturated hydrocarbon chain containing from 1 to 6 carbon atoms including, but not limited to, methyl, ethyl, n-propyl, iso-propyl, n-butyl, iso-butyl, sec-butyl, t-butyl, n-pentyl, n-hexyl, and the like. Advantageously, it is a methyl group.

The term "$(C_2-C_6)$alkenyl", as used in the present invention, refers to a straight or branched unsaturated hydrocarbon chain containing from 2 to 6 carbon atoms and comprising at least one double bond including, but not limited to, ethenyl, propenyl, butenyl, pentenyl, hexenyl and the like.

The term "$(C_2-C_6)$alkynyl", as used in the present invention, refers to a straight or branched unsaturated hydrocarbon chain containing from 2 to 6 carbon atoms and comprising at least one triple bond including, but not limited to, ethynyl, propynyl, butynyl, pentynyl, hexynyl and the like.

The term "$(C_1-C_6)$alkoxy", as used in the present invention, refers to a $(C_1-C_6)$alkyl group as defined above bound to the molecule via an oxygen atom, including, but not limited to, methoxy, ethoxy, n-propoxy, iso-propoxy, n-butoxy, iso-butoxy, sec-butoxy, t-butoxy, n-pentoxy, n-hexoxy, and the like. Advantageously, it is a methoxy group.

The term "$(C_3-C_7)$cycloalkyl", as used in the present invention, refers to a hydrocarbon ring having 3 to 7 carbon atoms including, but not limited to, cyclopropyl, cyclopentyl, cyclohexyl and the like.

The term "$(C_3-C_7)$cycloalkyl-$(C_1-C_6)$alkyl", as used in the present invention, refers to a $(C_3-C_7)$cycloalkyl group as defined above bound to the molecule via a $(C_1-C_6)$alkyl group as defined above. Advantageously, a $(C_3-C_7)$cycloalkyl-$(C_1-C_6)$alkyl group comprises a cyclopropyl, cyclopentyl or cyclohexyl moiety and a methyl or ethyl moiety.

The term "aryl", as used in the present invention, refers to an aromatic hydrocarbon group comprising preferably 6 to 10 carbon atoms and comprising one or more fused rings, such as, for example, a phenyl or naphtyl group. Advantageously, it is a phenyl group.

The term "aryl-$(C_1-C_6)$alkyl", as used in the present invention, refers to an aryl group as defined above bound to the molecule via a $(C_1-C_6)$alkyl group as defined above. In particular, an aryl-$(C_1-C_6)$alkyl group is a benzyl group.

The term "$(C_1-C_6)$alkyl-aryl", as used in the present invention, refers to a $(C_1-C_6)$alkyl group as defined above bound to the molecule via an aryl group as defined above. In particular, it can be a tolyl group ($CH_3Ph$).

The term "5- to 7-membered heterocycloalkyl" as used in the present invention refers to a saturated hydrocarbon cycle having 5 to 7 members and in which one or several, notably 1 to 3, such as 1 or 2, carbon atoms are each replaced with a nitrogen, oxygen or sulphur atom, preferably with a nitrogen or oxygen atom. It can be for example a pyrrolidinyl, tetrahydrofuranyl, tetrahydrothienyl, piperidinyl, tetrahydropyranyl, morpholinyl, piperazinyl or azepanyl group.

The term "(5- to 7-membered heterocycloalkyl)-$(C_1-C_6)$alkyl", as used in the present invention, refers to a 5- to 7-membered heterocycloalkyl group as defined above bound to the molecule via a $(C_1-C_6)$alkyl group as defined above. A (5- to 7-membered heterocycloalkyl)-$(C_1-C_6)$alkyl group can comprise for example a pyrrolidinyl, tetrahydrofuranyl, tetrahydrothienyl, piperidinyl, tetrahydropyranyl, morpholinyl, piperazinyl or azepanyl moiety and a methyl or ethyl moiety.

The term "heteroaryl" as used in the present invention refers to an aromatic group, having preferably 5 to 10 members, comprising one or more, notably one or two fused rings, in which the atoms of the ring(s) consist of one or more, advantageously 1 to 4, and more advantageously 1 or 2, heteroatoms selected from nitrogen, oxygen and sulphur atoms, the remainder being carbon atoms. A heteroaryl group can be notably thienyl, furanyl, pyrrolyl, indolyl, etc.

The term "heteroaryl-$(C_1-C_6)$alkyl", as used in the present invention, refers to a heteroaryl group as defined above bound to the molecule via a $(C_1-C_6)$alkyl group as defined above. A heteroaryl-$(C_1$-$C_6)$alkyl group can comprise for example a thienyl, furanyl, pyrrolyl or indolyl moiety and a methyl or ethyl moiety.

The term "halogen", as used in the present invention, refers to a fluorine, bromine, chlorine or iodine atom.

The term "protecting group", as used in the present invention, refers to a chemical group which selectively blocks a reactive site in a multifunctional compound so as to allow selectively performing a chemical reaction on another unprotected reactive site.

The term "O-Protecting group" as used in the present invention refers to a substituent which protects hydroxyl groups (OH) against undesirable reactions during synthetic procedures such as those O-protecting groups disclosed in "Greene's Protective Groups In Organic Synthesis", 4$^{th}$ edition, 2007, John Wiley & Sons, Hoboken, N.J. A hydroxyl group protected by a O-protecting group can be for example an ether, an ester, a carbonate, an acetal and the like. In particular, O-protecting groups can be a $(C_1$-$C_6)$alkyl optionally substituted with one or several (notably 1 to 3) halogen atoms (such as chlorine atoms), such as methyl, ethyl, tert-butyl or 2,2,2-trichloroethyl; an aryl-$(C_1$-$C_6)$ alkyl, such as a benzyl, the aryl moiety being optionally substituted with one or several methoxy groups, such as benzyl (Bn) or p-methoxybenzyl (PMB); a trityl derivative of formula —$CAr_1Ar_2Ar_3$ such as triphenylmethyl (also called trityl—Tr), (4-methoxyphenyl)diphenylmethyl (also called methoxytrityl—NMT) or bis-(4-methoxyphenyl)phenylmethyl (also called dimethoxytrityl—DMT); a substituted methyl group of formula —$CH_2OR_{GP2}$ or —$CH_2SR_{GP2}$ (in particular —$CH_2OR_{GP2}$), for example, methoxymethyl (MOM), benzyloxymethyl, 2-methoxyethoxymethyl (MEM), 2-(trimethylsilyl)ethoxymethyl or methylthiomethyl; a substituted ethyl group of formula —$CH_2CH_2OR_{GP2}$ or —$CH_2CH_2SR_{GP2}$ (in particular —$CH_2CH_2OR_{GP2}$), for example, ethoxyethyl (EE); a silyl group of formula —$SiR_{GP3}R_{GP4}R_{GP5}$, for example, trimethylsilyl (TMS), triethylsilyl (TES), t-butyldimethylsilyl (TBS or TBDMS) and t-butyldiphenylsilyl (TBDPS); a carbonylated group of formula —CO—$R_{GP6}$ such as acetyl (Ac), pivaloyl (Piv or Pv) or benzoyl (Bz) or of formula —$CO_2$—$R_{GP7}$ such as allyloxycarbonyl (Alloc) or 9-fluorenylmethyloxycarbonyl (Fmoc); or a tetrahydropyranyl

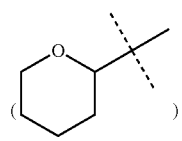

(THP) or tetrahydrofuranyl

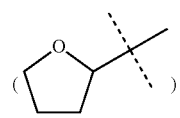

group;
with $Ar_1$, $Ar_2$ and $Ar_3$ representing, independently from one another, an aryl, such as a phenyl, optionally substituted with one or several methoxy groups; $R_{GP2}$ representing a $(C_1$-$C_6)$alkyl (such as methyl or ethyl) optionally substituted with an aryl (such as phenyl), a $(C_1$-$C_6)$alkoxy (such as methoxy) or a trialkylsilyl group (such as $SiMe_3$); $R_{GP3}$, $R_{GP4}$ and $R_{GP5}$ representing, independently from one another, a $(C_1$-$C_6)$alkyl or aryl (such as phenyl) group; and $R_{GP6}$ and $R_{GP7}$ representing, independently of each other, a $(C_1$-$C_6)$alkyl, a $(C_2$-$C_6)$alkenyl, an aryl, an aryl-$(C_1$-$C_6)$alkyl or a 9-fluorenylmethyl group.

In particular, it will be a methyl, benzyl, acetyl or methoxymethyl group.

The term "N-protecting group", as used in the present invention, refers to those groups intended to protect an amine function (notably a primary amine function) against undesirable reactions during synthetic procedures. Commonly used N-protecting groups are disclosed in "Greene's Protective Groups In Organic Synthesis", 4$^{th}$ edition, 2007, John Wiley & Sons, Hoboken, N.J. An amine function protected by a N-protecting group can be a carbamate, an amide, a sulfonamide, an N-alkyl derivative, an amino acetal derivative, a N-benzyl derivative, an imine derivative, an enamine derivative or a N-heteroatom derivative. In particular, N-protecting groups can be formyl; an aryl, such as a phenyl, optionally substituted with one or several methoxy groups such as p-methoxyphenyl (PMP); an aryl-$(C_1$-$C_6)$ alkyl, such as a benzyl, the aryl moiety being optionally substituted with one or several methoxy groups, such as benzyl (Bn), p-methoxybenzyl (PMB) or 3,4-dimethoxybenzyl (DMPM); —CO—$R_{GP1}$ such as acetyl (Ac), pivaloyl (Piv or Pv), benzoyl (Bz) or p-methoxybenzylcarbonyl (Moz); —$CO_2$—$R_{GP1}$ such as tbutyloxycarbonyl (Boc), trichloroethoxycarbonyl (TROC), allyloxycarbonyl (Alloc), benzyloxycarbonyl (Cbz or Z) or 9-fluorenylmethyloxycarbonyl (Fmoc); —$SO_2$—$R_{GP1}$ such as phenylsulfonyl, tosyl (Ts or Tos) or 2-nitrobenzenesulfonyl (also called nosyl—Nos or Ns); and the like, with $R_{GP1}$ representing a $(C_1$-$C_6)$ alkyl optionally substituted with one or several halogen atoms such as F or Cl; a $(C_2$-$C_6)$alkenyl such as an allyl; an aryl, such as a phenyl, optionally substituted with one or several groups chosen among OMe (methoxy) and $NO_2$ (nitro); an aryl-$(C_1$-$C_6)$alkyl, such as a benzyl, the aryl moiety being optionally substituted with one or several methoxy groups; or a 9-fluorenylmethyl group.

In particular, it can be a t-butyloxycarbonyl, benzyloxycarbonyl or 9-fluorenylmethyloxycarbonyl group.

According to a first embodiment, $R_1$ represents a hydrogen atom and $R_2$ represents a hydrogen atom, $OSiR_3R_4R_5$, $OR_6$, $OC(O)R_7$, $OCO_2R_8$, $OC(O)NR_9R_{10}$, $OP(O)(OR_{11})_2$, or $OSO_3R_{12}$; or $R_1$ and $R_2$ form together an oxo group (=O); or $R_1$ and $R_2$ are linked together by a chain of formula —$O(CH_2)_nO$—.

Advantageously, $R_1$ represents a hydrogen atom and $R_2$ represents a hydrogen atom, $OR_6$, $OC(O)R_7$, $OCO_2R_8$, or $OC(O)NR_9R_{10}$; or $R_1$ and $R_2$ form together an oxo group (=O); or $R_1$ and $R_2$ are linked together by a chain of formula —$O(CH_2)_nO$—.

In particular, $R_1$ represents a hydrogen atom and $R_2$ represents a hydrogen atom or an $OR_6$ group; or $R_1$ and $R_2$ form together an oxo group (=O); or $R_1$ and $R_2$ are linked together by a chain of formula —$O(CH_2)_nO$—.

Preferably, $R_1$ represents a hydrogen atom and $R_2$ represents a hydrogen atom or an OH group; or $R_1$ and $R_2$ form together an oxo group (=O); or $R_1$ and $R_2$ are linked together by a chain of formula —$O(CH_2)_nO$—, with n as defined above and preferably with n=2.

According to a first embodiment, $R_1$ and $R_2$ represent, independently from each other, a hydrogen atom, $OSiR_3R_4R_5$, $OR_6$, $OC(O)R_7$, $OCO_2R_8$, $OC(O)NR_9R_{10}$, $OP(O)(OR_{11})_2$, or $OSO_3R_{12}$.

Notably, $R_1$ represents a hydrogen atom and $R_2$ represents a hydrogen atom, $OSiR_3R_4R_5$, $OR_6$, $OC(O)R_7$, $OCO_2R_8$, $OC(O)NR_9R_{10}$, $OP(O)(OR_{11})_2$, or $OSO_3R_{12}$.

Advantageously, $R_1$ represents a hydrogen atom and $R_2$ represents a hydrogen atom, $OR_6$, $OC(O)R_7$, $OCO_2R_8$, or $OC(O)NR_9R_{10}$.

In particular, $R_1$ represents a hydrogen atom and $R_2$ represents a hydrogen atom or an $OR_6$ group.

Preferably, $R_1$ represents a hydrogen atom and $R_2$ represents a hydrogen atom or an OH group.

$X_1$, $X_2$, $X_3$, $X_4$, $X_5$ represent, independently from one another, a hydrogen atom, $OSiR_{13}R_{14}R_{15}$, $OR_{16}$, $OC(O)R_{17}$, $OCO_2R_{18}$, $OC(O)NR_{19}R_{20}$, $OP(O)(OR_{21})_2$, or $OSO_3R_{22}$.

Advantageously, $X_1$, $X_2$, $X_3$, $X_4$, $X_5$ represent, independently from one another, a hydrogen atom, $OR_{16}$, $OC(O)R_{17}$, $OCO_2R_{18}$, $OC(O)NR_{19}R_{20}$, or $OSO_3R_{22}$.

In particular, $X_1$, $X_2$, $X_3$, $X_4$, $X_5$ represent, independently from one another, a hydrogen atom, $OR_{16}$, $OC(O)R_{17}$, $OCO_2R_{18}$, or $OC(O)NR_{19}R_{20}$.

Preferably, $X_1$, $X_2$, $X_3$, $X_4$, $X_5$ represent, independently from one another, a hydrogen atom, $OR_{16}$, $OC(O)R_{17}$, or $OCO_2R_{18}$.

Most preferably, $X_1$, $X_2$, $X_3$, $X_4$, $X_5$ represent, independently from one another, a hydrogen atom, $OR_{16}$ or $OC(O)R_{17}$.

According to an advantageous embodiment, $X_1$, $X_2$, $X_4$ and $X_5$ each represent a hydrogen atom. In this case, $X_3$ preferably does not represent a hydrogen atom.

Thus, $X_1$, $X_2$, $X_4$ and $X_5$ will each represent advantageously a hydrogen atom, whereas $X_3$ will represent $OSiR_{13}R_{14}R_{15}$, $OR_{16}$, $OC(O)R_{17}$, $OCO_2R_{18}$, $OC(O)NR_{19}R_{20}$, $OP(O)(OR_{21})_2$, or $OSO_3R_{22}$.

Advantageously, $X_1$, $X_2$, $X_4$ and $X_5$ each represent advantageously a hydrogen atom, whereas $X_3$ represents $OR_{16}$, $OC(O)R_{17}$, $OCO_2R_{18}$, $OC(O)NR_{19}R_{20}$, or $OSO_3R_{22}$.

In particular, $X_1$, $X_2$, $X_4$ and $X_5$ each represent advantageously a hydrogen atom, whereas $X_3$ represents $OR_{16}$, $OC(O)R_{17}$, $OCO_2R_{18}$, or $OC(O)NR_{19}R_{20}$.

Preferably, $X_1$, $X_2$, $X_4$ and $X_5$ each represent advantageously a hydrogen atom, whereas $X_3$ represents $OR_{16}$, $OC(O)R_{17}$, or $OCO_2R_{18}$.

Most preferably, $X_1$, $X_2$, $X_4$ and $X_5$ each represent advantageously a hydrogen atom, whereas $X_3$ represents $OR_{16}$ or $OC(O)R_{17}$.

According to a particular embodiment:
$R_1$ represents a hydrogen atom,
$R_2$ represents a hydrogen atom, $OSiR_3R_4R_5$, $OR_6$, $OC(O)R_7$, $OCO_2R_8$, $OC(O)NR_9R_{10}$, $OP(O)(OR_{11})_2$, or $OSO_3R_{12}$, or
$R_1$ and $R_2$ form together an oxo group (=O), or
$R_1$ and $R_2$ are linked together by a chain of formula —O(CH$_2$)$_n$O—,
$X_1$, $X_2$, $X_4$ and $X_5$ each represent a hydrogen atom, and
$X_3$ represents $OSiR_{13}R_{14}R_{15}$, $OR_{16}$, $OC(O)R_{17}$, $OCO_2R_{18}$, $OC(O)NR_{19}R_{20}$, $OP(O)(OR_{21})_2$, or $OSO_3R_{22}$, According to an advantageous embodiment:
$R_1$ represents a hydrogen atom,
$R_2$ represents a hydrogen atom, $OR_6$, $OC(O)R_7$, $OCO_2R_8$ or $OC(O)NR_9R_{10}$, or
$R_1$ and $R_2$ form together an oxo group (=O), or
$R_1$ and $R_2$ are linked together by a chain of formula —O(CH$_2$)$_n$O—,
$X_1$, $X_2$, $X_4$ and $X_5$ each represent a hydrogen atom, and
$X_3$ represents $OR_{16}$, $OC(O)R_{17}$, $OCO_2R_{18}$, $OC(O)NR_{19}R_{20}$, or $OSO_3R_{22}$, According to a preferred embodiment:
$R_1$ represents a hydrogen atom,
$R_2$ represents a hydrogen atom or an $OR_6$ group (such as an OH group), or
$R_1$ and $R_2$ form together an oxo group (=O), or
$R_1$ and $R_2$ are linked together by a chain of formula —O(CH$_2$)$_n$O—,
$X_1$, $X_2$, $X_4$ and $X_5$ each represent a hydrogen atom, and
$X_3$ represents $OR_{16}$, $OC(O)R_{17}$, $OCO_2R_{18}$, $OC(O)NR_{19}R_{20}$, or $OSO_3R_{22}$; advantageously $OR_{16}$, $OC(O)R_{17}$, $OCO_2R_{18}$, or $OC(O)NR_{19}R_{20}$; preferably $OR_{16}$, $OC(O)R_{17}$ or $OCO_2R_{18}$; most preferably $OR_{16}$ or $OC(O)R_{17}$.

In the above definitions of $R_1$, $R_2$, $X_1$, $X_2$, $X_3$, $X_4$ and $X_5$ (including the particular and preferred embodiments):
$R_6$ and $R_{16}$ advantageously represent, independently from one another, a hydrogen atom; a O-protecting group; or a ($C_1$-$C_6$)alkyl, ($C_3$-$C_7$)cycloalkyl, aryl, ($C_3$-$C_7$)cycloalkyl-($C_1$-$C_6$)alkyl, or aryl-($C_1$-$C_6$)alkyl group, said group being optionally substituted by one or several groups selected from a halogen atom, a ($C_1$-$C_6$)alkyl group and a ($C_1$-$C_6$)alkoxy group, $R_7$, $R_8$, $R_{17}$ and $R_{18}$ advantageously represent, independently from one another, a ($C_1$-$C_6$)alkyl, ($C_3$-$C_7$)cycloalkyl, aryl, ($C_3$-$C_7$)cycloalkyl-($C_1$-$C_6$)alkyl, or aryl-($C_1$-$C_6$)alkyl group, said group being optionally substituted by one or several groups selected from a halogen atom, a ($C_1$-$C_6$)alkyl group and a ($C_1$-$C_6$)alkoxy group, and $R_9$, $R_{10}$, $R_{19}$ and $R_{20}$ represent, independently from one another, a hydrogen atom; a N-protecting group; or a ($C_1$-$C_6$)alkyl, ($C_3$-$C_7$)cycloalkyl, aryl, ($C_3$-$C_7$)cycloalkyl-($C_1$-$C_6$)alkyl, or aryl-($C_1$-$C_6$)alkyl group, said group being optionally substituted by one or several groups selected from a halogen atom, a ($C_1$-$C_6$)alkyl group and a ($C_1$-$C_6$)alkoxy group.

In the above definitions of $R_1$, $R_2$, $X_1$, $X_2$, $X_3$, $X_4$ and $X_5$ (including the particular and preferred embodiments):
$R_6$, $R_9$, $R_{10}$, $R_{16}$, $R_{19}$ and $R_{20}$, preferably represent, independently from one another, a hydrogen atom; or a ($C_1$-$C_6$)alkyl, aryl, or aryl-($C_1$-$C_6$)alkyl group, said group being optionally substituted by one or several groups selected from a halogen atom, a ($C_1$-$C_6$)alkyl group and a ($C_1$-$C_6$)alkoxy group, notably selected from a ($C_1$-$C_6$)alkyl group and a ($C_1$-$C_6$)alkoxy group, and $R_7$, $R_8$, $R_{17}$ and $R_{18}$ preferably represent, independently from one another, a ($C_1$-$C_6$)alkyl, aryl, or aryl-($C_1$-$C_6$)alkyl group, said group being optionally substituted by one or several groups selected from a halogen atom, a ($C_1$-$C_6$)alkyl group and a ($C_1$-$C_6$)alkoxy group, notably selected from a ($C_1$-$C_6$)alkyl group and a ($C_1$-$C_6$)alkoxy group.

The compounds of formula (I) can be chosen from the following compounds:

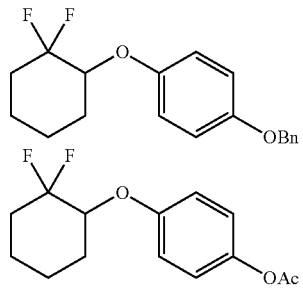

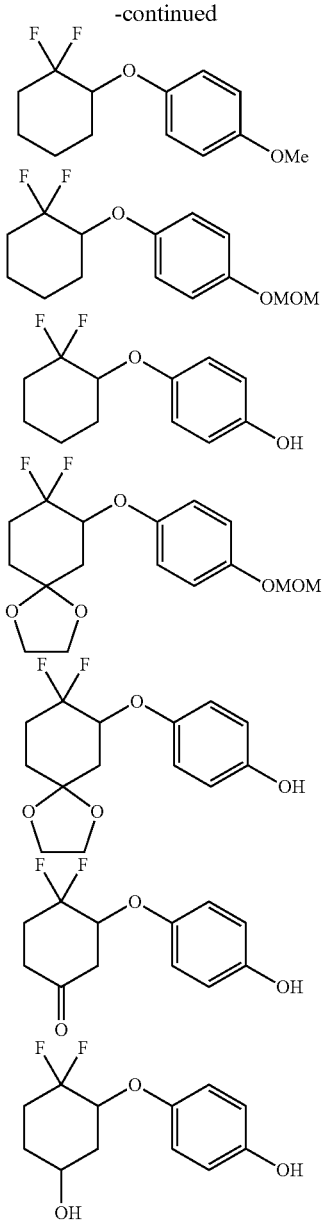

and the cosmetically and pharmaceutically salts thereof.

The present invention relates also to a cosmetic or pharmaceutical composition, more particularly a cosmetic or dermatological composition, comprising at least one compound of formula (I) according to the invention and at least one cosmetically or pharmaceutically acceptable excipient.

Such a composition is more particularly intended to be applied topically, in particular on the skin, such as a human skin.

Such a composition can thus be in the form of a lotion, a foam, a gel, a dispersion, a suspension, a spray, a serum, a cream, an emulsion, a body milk, or also a mask.

The composition of the invention can also comprise one or more additive(s), such as antioxidants, emollients, humectants, thickening agents, fragrances, preservatives, pigments or colorants, or opacifiers. Such additives are conventional to those of skill in the art.

Examples of these additives are listed below as well as in the International Cosmetic Ingredient Dictionary and Handbook, eds. Wenninger and McEwen (The Cosmetic, Toiletry, and Fragrance Assoc., Washington, D.C., 7@th Edition, 1997) (hereinafter "ICT Handbook").

Antioxidants can be used to protect ingredients of the composition from oxidizing agents that are included within or come in contact with the composition. Examples of antioxidants include ascorbyl palmitate, butylated hydroxyanisole, butylated hydroxytoluene, potassium propyl gallate, octyl gallate, dodecyl gallate, phenyl-α-napthyl-amine, and tocopherols such as α-tocopherol.

Emollients are agents that soften and smooth the skin. Examples of emollients include oils and waxes such as microcrystaline wax, polyethylene, triglyceride esters such as those of castor oil, cocoa butter, safflower oil, corn oil, olive oil, cod liver oil, almond oil, palm oil, squalene, and soybean oil, acetylated monoglycerides, ethoxylated glycerides, fatty acids, alkyl esters of fatty acids, alkenyl esters of fatty acids, fatty alcohols, fatty alcohol ethers, etheresters, lanolin and derivatives of lanolin, polyhydric alcohol esters, wax esters such as beeswax, vegetable waxes, phospholids, and sterols, isopropyl palmitate or glyceryl stearate, and in particular almond oil or fatty alcohols such as cetyl, stearyl and/or myristyl alcohols.

Siloxanes are particularly preferred emollient. Siloxanes that may be used in the present invention include, but are not limited to, dimethicone, cyclomethicone, phenyl trimethicone, phenyl dimethicone, cetyl dimethicone, stearyl dimethicone, amodimethicone, $C_{30-45}$ alkyl dimethicone, $C_{30-45}$ Alkyl Methicone, Cetearyl methicone, dimethicone copolyol, cyclopentasiloxane, cyclohexasiloxane or any combinations thereof. In particular, amodimethicone could be used as emollient in the present invention.

Humectants are used to increase and maintain moisture in the skin. Examples of humectants include propylene glycol, butylene glycol, polyethylene glycol (PEG) (such as PEG-4 to PEG-32), glycerol (also called glycerin), sorbitol, xylitol, maltitol, mannitol, polydextrose, hyaluronic acid and its salts (such as sodium or potassium salt), urea, aloe vera, honey, etc.

Thickening agents are used to increase the viscosity and thickness of the composition. Examples of thickening agents include lipid thickening agents such as Cetyl Alcohol, Stearyl Alcohol, Myristyl Alcohol, Carnauba Wax, or Stearic acid; naturally derived thickening agents such as Cellulose derivatives like Hydroxyethylcellulose, Guar gum, Locust Bean Gum, Xanthan Gum, or Gelatin; mineral thickening agents such as Silica, Bentonite, or Magnesium Aluminum Silicate; synthetic thickening agents such as Carbomer; ionic thickening agents such as NaCl.

Examples of fragrances or perfume include peppermint, rose oil, rose water, aloe vera, clove oil, menthol, camphor, *eucalyptus* oil, and other plant extracts. To eliminate certain odours from compositions, masking agents may be used Preservatives can be used to protect the composition from degradation.

Examples of preservatives include phenoxyethanol, methylparaben, benzalkonium chloride, benzethonium chloride, propyl paraben, benzoic acid, benzyl alcohol, and mixtures thereof such as liquipar oil. In particular, it can be phenoxyethanol, methylparaben or a mixture thereof.

Pigments or colorants are used to modify the color of the composition, such as to obtain a white composition. It can be in particular titanium dioxide.

Opacifiers, such as titanium oxide, are used in clear or transparent composition in order to render it opaque.

The present invention relates also to the cosmetic use of a compound of formula (I) according to the invention, in particular as depigmenting, lightening, bleaching or whitening agent, more particularly for the skin, such as a human skin.

The invention relates also to the cosmetic use of a cosmetic composition according to the invention, in particular as a depigmenting, lightening, bleaching or whitening composition, more particularly intended to be applied topically on the skin, such as a human skin.

The invention concerns also the use of a compound of formula (I) according to the invention for the preparation of a cosmetic composition, intended notably for depigmenting, lightening, bleaching or whitening the skin, such as a human skin.

The invention concerns also a compound of formula (I) according to the invention for use as a depigmenting, lightening, bleaching or whitening agent, more particularly for the skin, such as a human skin.

The invention concerns also a method for depigmenting, lightening, bleaching or whitening the skin, such as a human skin, by applying on said skin an efficient amount of a compound of formula (I) according to the invention or of a cosmetic composition according to the invention to a person in need thereof.

The present invention relates also to a compound of formula (I) according to the invention for use as a drug, notably in the treatment of pigmentation disorders, more particularly by topical application on the skin, such as a human skin.

The invention relates also to a pharmaceutical composition, in particular a dermatological composition, according to the invention for use as a drug, notably in the treatment of pigmentation disorders, more particularly by topical application on the skin, such as a human skin.

The invention concerns also the use of a compound of formula (I) according to the invention for the preparation of a pharmaceutical composition, in particular a dermatological composition, intended notably for the treatment of pigmentation disorders, more particularly by topical application on the skin, such as a human skin.

The invention concerns also the use of a compound of formula (I) according to the invention for the treatment of pigmentation disorders, more particularly by topical application on the skin, such as a human skin.

The invention concerns also a method for treating the pigmentation disorders of the skin, such as a human skin, by applying on said skin an efficient amount of a compound of formula (I) according to the invention or of a pharmaceutical composition, in particular a dermatological composition, according to the invention to a person in need thereof.

The pigmentation disorders will be more particularly a hyperpigmentation including *lentigo*, melasma, ephelides, postinflammatory hyperpigmentation, and hyperpigmentation causes by drugs, chemicals or sun.

The present invention relates also to a compound of formula (I) according to the invention for use as an antioxidant, in particular to inhibit or to reduce oxidative stress, notably due to UV, more particularly in skin.

The present invention concerns also the use of a compound of formula (I) according to the invention, as an antioxidant, in particular to inhibit or to reduce oxidative stress, notably due to UV, more particularly in skin.

The invention concerns also a method for inhibiting or reducing oxidative stress, notably due to UV, more particularly in the skin, comprising the administration, in particular the topical administration, of an efficient amount of a compound of formula (I) according to the invention to a person in need thereof.

The present invention relates also to a method for the preparation of a compound of formula (I) according to the invention comprising:

(1) the fluorination of the ketone function of a compound of the following formula (II):

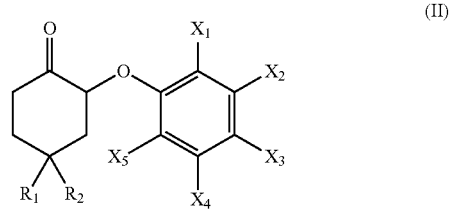

in which $R_1$, $R_2$, $X_1$, $X_2$, $X_3$, $X_4$ and $X_5$ are as defined previously and are optionally in a protected form, (2) the deprotection of the $R_1$, $R_2$, $X_1$, $X_2$, $X_3$, $X_4$ and/or $X_5$ groups when they are in a protected form, and (3) optionally the salification of the compound of formula (I) obtained in previous step (1) or (2) to give a cosmetically or pharmaceutically acceptable salt of the compound of formula (I).

Step (1)—Fluorination:

This fluorination step is performed in the presence of a fluorinating agent and is well-known to the one skilled in the art. The fluorinating agent can be for example DAST (diethylaminosulfur trifluoride—$Et_2N$—$SF_3$), XtalFluor-E® (diethylaminodifuorosulfinium tetraftuoroborate—

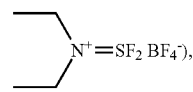

Deoxo-Fluor® (bis(2-methoxyethyl)aminosulfur trifluoride—$(MeOCH_2CH_2)_2N$—$SF_3$), Morpho-DAST (morpholinosulfur trifluoride—

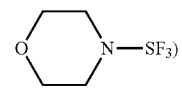

or Fluolead™ (4-tert-butyl-2,6-dimethylphenylsulfur trifluoride—

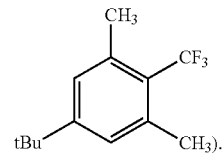

The fluorinating agent will be more particularly DAST or XtalFluor-E®.

The reaction conditions are well-known to the one skilled in the art and are exemplified in the examples below. For example, the reaction can be carried out in dichloromethane (DCM) as solvent. Triethylamine trihydrofluoride can be added to the reaction medium.

The compound of formula (II) can be obtained by a nucleophilic substitution between a compound of the following formula (III) and a compound of the following formula (IV):

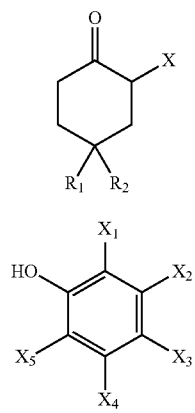

(III)

(IV)

in which X represents a leaving group and $R_1$, $R_2$, $X_1$, $X_2$, $X_3$, $X_4$ and $X_5$ are as defined previously and are optionally in a protected form.

The term "leaving group" as used in the present invention refers to a chemical group which can be easily replaced with a nucleophile during a nucleophile substitution reaction, the nucleophile being in the present case a phenol derivative, i.e. a molecule comprising a phenyl moiety carrying a group OH. Such a leaving group can be in particular a halogen atom or a sulfonate. The sulfonate is in particular a group —$OSO_2$—$R_{LG}$ with $R_{LG}$ representing a ($C_1$-$C_6$)alkyl, aryl, aryl-($C_1$-$C_6$)alkyl or ($C_1$-$C_6$)alkyl-aryl group, the said group being optionally substituted with one or several halogen atoms such as fluorine atoms. The sulfonate can be notably a mesylate ($CH_3$—$S(O_2)O$—), a triflate ($CF_3$—$S(O)_2O$—) or a tosylate (p-Me-$C_6H_4$—$S(O)_2O$—).

X will represent more particularly a halogen atom, such as Cl or Br, as a leaving group.

The reaction conditions of the nucleophilic substitution are well-known to the one skilled in the art and are exemplified in the examples below. This nucleophilic substitution will be advantageously performed in the presence of a base such as $K_2CO_3$, $Cs_2CO_3$, $Et_3N$, KOH, or NaH, and preferably $K_2CO_3$. For example, the nucleophilic substitution can be carried out in acetone, toluene or dimethylformamide (DMF) or also in acetonitrile as solvent, notably at a temperature above 50° C., such as at reflux.

The compound of formula (II) can be obtained also by oxidation of the OH group of a compound of the following formula (V):

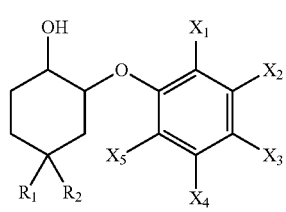

(V)

in which $R_1$, $R_2$, $X_1$, $X_2$, $X_3$, $X_4$ and $X_5$ are as defined previously and are optionally in a protected form.

The reaction conditions of this oxidation are well-known to the one skilled in the art. This oxidation is performed in the presence of an oxidizing agent such as Dess Martin reagent.

The compound of formula (V) can be obtained by a hydroboration-oxidation sequence from a compound of the following formula (VI):

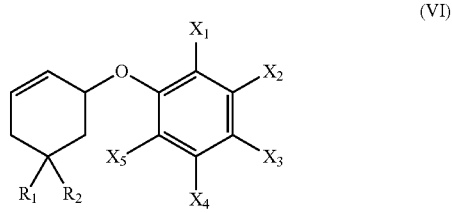

(VI)

in which $R_1$, $R_2$, $X_1$, $X_2$, $X_3$, $X_4$ and $X_5$ are as defined previously and are optionally in a protected form.

The reaction conditions of this hydroboration-oxidation sequence are well-known to the one skilled in the art. The hydroboration step can be performed in the presence of a hydroborane (hydroboration reagent) such as $BH_3$, 9-borabicyclo[3.3.1]nonane (9-BBN), catecholborane or disiamylborane. The oxidation step can be performed in the presence of an oxidizing agent such as hydrogen peroxide. For example, this sequence can be carried out in tetrahydrofurane (THF) as solvent.

The compound of formula (VI) can be obtained by a Mitsunobu reaction between a compound of the following formula (VII) and a compound of the following formula (IV):

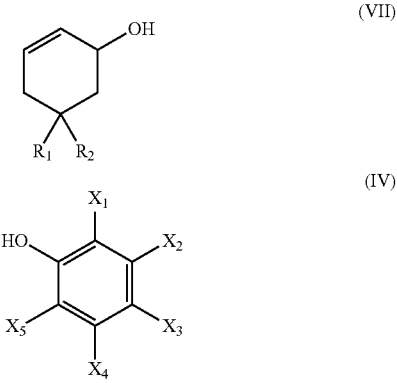

(VII)

(IV)

in which $R_1$, $R_2$, $X_1$, $X_2$, $X_3$, $X_4$ and $X_5$ are as defined previously and are optionally in a protected form.

The reaction conditions of the Mitsunobu reaction are well-known to the one skilled in the art. Such a reaction can be performed in the presence of diethyl azodicarboxylate (DEAD), bis(2-methoxyethyl) azodicarboxylate (DMEAD) or 1,1'-(azodicarbonyl)dipiperidine (ADDP) and of triphenylphosphine ($PPh_3$). For example, the Mitsunobu reaction can be carried out in tetrahydrofurane (THF) as solvent.

The compounds of formula (III), (IV) and (VII) are commercially available or easily prepared by the one skilled in the art by well-known synthesis methods.

Step (2)—Deprotection:

The deprotection steps aim to remove the protecting group(s) used in step (1) to protect the $R_1$, $R_2$, $X_1$, $X_2$, $X_3$, $X_4$ and/or $X_5$ groups. The deprotection conditions depend on the nature of the protecting group(s) used and are well-known to the one skilled in the art. The deprotection conditions are notably described in "Greene's Protective Groups In Organic Synthesis", $4^{th}$ edition, 2007, John Wiley & Sons, Hoboken, N.J.

Advantageously, when $R_1$, $R_2$, $X_1$, $X_2$, $X_3$, $X_4$ and/or $X_5$ represent a hydroxyl group (OH), they will be protected before performing step (1). The hydroxyl group can be protected by an O-protecting group as defined previously, and in particular with a methyl, benzyl, acetyl or methoxymethyl group.

The benzyl group can be deprotected by hydrogenolysis, notably in the presence of Pd/C under a hydrogen atmosphere.

The acetyl group can be deprotected in an acidic or basic medium.

The methoxymethyl group can be deprotected by hydrolysis in an acidic medium, notably in the presence of trifluoroacetic acid (TFA).

Step (3)—Salification:

The salification step can be carried out by methods well known to the one skilled in the art, in particular by reaction of the compound of formula (I) obtained in previous step (1) or (2) with a pharmaceutically acceptable acid (organic or inorganic acid) or base (organic or inorganic acid) as defined previously.

Step (3) can be carried out notably by adding the required acid or base in the reaction medium at the end of step (1) or (2), without isolating the intermediate compound in a neutral form. However, it is also possible to isolate and/or purify the intermediate compound in a neutral form before performing the salification step.

The method described above is represented notably on Scheme 1 below.

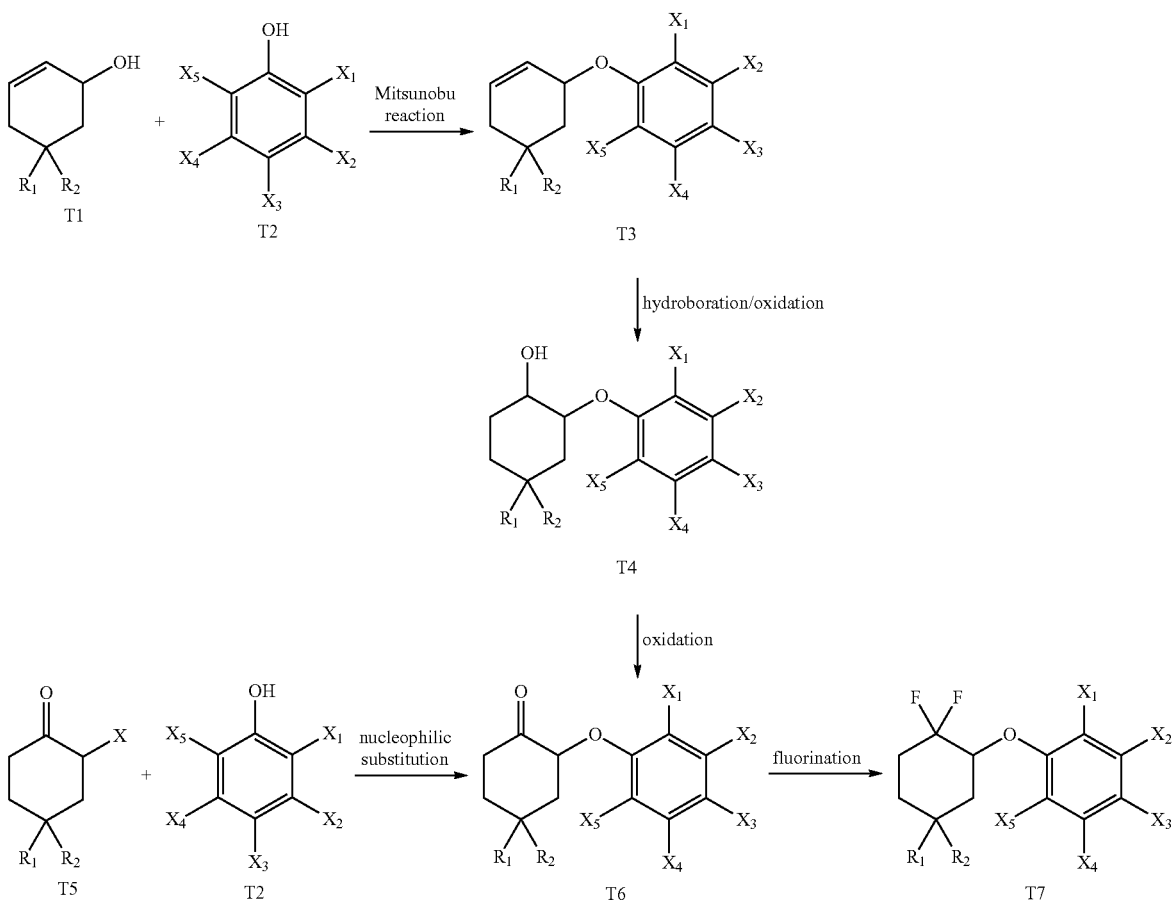

Scheme 1

The compound T6 can be obtained through two different approaches. The first one, involves a Mitsunobu reaction between the compounds T1 and T2 using for example ADDP and P(nBu)$_3$ followed by a hydroboration/oxidation sequence of the double bond of the compound T3 and an oxidation step with Dess Martin reagent. The second approach includes a nucleophilic substitution in the presence of a cyclohexenone T5 comprising a leaving group such as a halo-cyclohexenone, a phenol derivative T2 and a base such as $K_2CO_3$, $Cs_2CO_3$, $Et_3N$, KOH, or NaH, preferentially $K_2CO_3$.

The compounds T1, T2, T5 (wherein X=halogen) can be commercially available or prepared with methods well known to the person skilled in the art.

Then from the compound T6, a fluorination step with a fluorinating agent such as DAST or XtalFluor-E® gives the compound T7.

In some cases, the $R_1$, $R_2$, $X_1$, $X_2$, $X_3$, $X_4$ and $X_5$ groups should be first transformed into unreactive groups under the steps conditions to protect them, particularly if $R_1$, $R_2$, $X_1$, $X_2$, $X_3$, $X_4$ and/or $X_5$ represent an OH group, such groups being reactive in the synthesis conditions. In these cases, a final deprotection step will be required to obtain the compounds of formula (I) comprising unprotected $R_1$, $R_2$, $X_1$, $X_2$, $X_3$, $X_4$ and $X_5$ groups.

Further protection, deprotection, substitution and/or functionalization steps can be carried out in the process described above, such steps and their reaction conditions being well known to the one skilled in the art.

Scheme 2 describes notably a process to introduce ($R_1$, $R_2$) groups representing =O; —O(CH$_2$)$_2$O—; or (H, OH). Further functionalization/substitution steps well known to the one skilled in the art will allow introducing other substituting ($R_1$, $R_2$) groups.

The present invention is illustrated by the following non-limiting examples and FIGURE.

BRIEF DESCRIPTION OF THE FIGURE

FIG. 1 represents the inhibition of human tyrosinase kinetics of compounds 11 and 16 at 1.12 mM.

EXAMPLES

The following abbreviates have been used in the examples.

Ac: Acetyl (COCH$_3$)
ACN: Acetonitrile
ADDP: 1,1'-(Azodicarbonyl)dipiperidine

Scheme 2

The compound T15 (wherein X represents a leaving group such as a halogen atom) is synthesized according to a procedure described in the literature (*Chem. Eur. J.* 2007, 13, 3739-3756). This compound T15 can be obtained in two steps including the formation of a trimethylsilylenol ether from commercially available cycloketone, followed by a halogenation. Then, the compound T16 is formed by a nucleophilic substitution between T15 and T2 in the presence of a base such as K$_2$CO$_3$. The fluorination of the compound T16 gives the compound T17. Finally, an appropriate deprotection of the compound T17 with acidic condition provides T18, which is engaged in a reductive step to afford the compound T19.

The final compound obtained can be separated from the reaction medium by methods well known to the person skilled in the art, such as by extraction, evaporation of the solvent or by precipitation or crystallisation (followed by filtration).

The compound thus obtained can be also purified if necessary by methods well known to the person skilled in the art, such as by recrystallisation, by distillation, by chromatography on a column of silica gel or by high performance liquid chromatography (HPLC).

AP: Affinity-purification
aq.: aqueous
DAST: Diethylaminosulphurtrifluoride
DCM: Dichloromethane
DIPEA: N,N-Diisopropylethylamine
eq: Equivalent
GC/MS: Gas chromatography-mass spectrometry
HPLC: High Performance Liquid Chromatography
LC-MS/MS: Liquid chromatography coupled to tandem mass spectrometry
LLOQ: Lower limit of quantification
MOM: Methoxymethyl
NMR: Nuclear Magnetic Resonance
OD: Optical density
RT: Room temperature
sat.: saturated
TLC: Thin Layer Chromatography
UV/DAD: Ultraviolet diode array detector

1. Preparation of the Compounds According to the Invention

Synthesis of Intermediate Compound 1

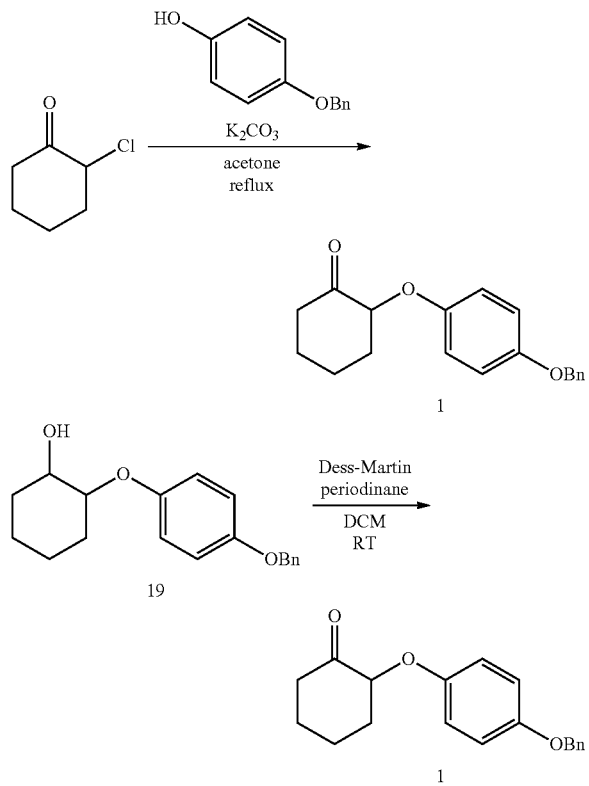

Route 1:

Under inert atmosphere, K$_2$CO$_3$ (0.42 g, 3.02 mmol, 2 eq) was added to a mixture of o-chlorocyclohexanone (0.20 g, 1.5 mmol, 1 eq) and p-benzyloxyphenol (0.45 g, 2.26 mmol, 1.5 eq) in acetone (3 mL) and the reaction mixture was refluxed for 1 h. The reaction can also be performed in acetonitrile at a temperature of 60° C. The reaction was monitored by TLC (cyclohexane/ethyl acetate 8:2—stain: vanillin). Water (5 mL) and diethyl ether (10 mL) were then added at room temperature and the aqueous layer was extracted with diethyl ether (3×20 mL). The combined organic layer was then washed with 1N NaOH (4×20 mL), dried over sodium sulfate, filtered and concentrated. The crude brown oil was purified by flash chromatography (Biotage® SNAP 25 g, cyclohexane/ethyl acetate 98:2 to 80:20) to afford intermediate compound 1 (0.28 g, 62%) as a white solid. Compound 1 can also be obtained by recrystallization in a mixture of heptane/isopropanol (5/1).

Route 2:

Under inert atmosphere, Dess-Martin periodinane (42.6 mg, 0.101 mmol, 1.5 eq) was added to a solution of intermediate compound 19 (20 mg, 0.067 mmol, 1 eq) in dry DCM (200 μL). The mixture was stirred at 25° C. for 2.5 hours before aq. NaOH 1N was added. The mixture was then extracted with DCM (3×10 mL). The organic layers were combined, dried over sodium sulfate and concentrated to give intermediate compound 1 (16 mg, 81%) as a white solid.

Mass (AP+): 297.1 [M+H]$^+$; 314.1 [M+NH$_4$]$^+$; 319.1 [M+Na]$^+$; 335.1 [M+K]$^+$; 360.1 [M+Na+CH$_3$CN]$^+$; 615.2 [2M+Na]$^+$.

Synthesis of Intermediate Compound 2

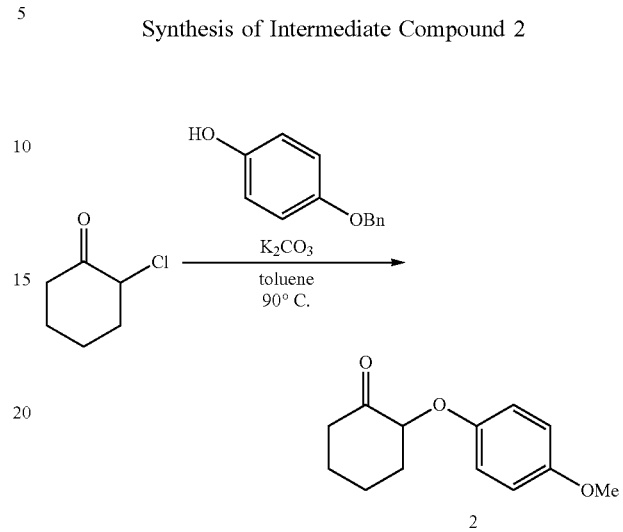

Under inert atmosphere, K$_2$CO$_3$ (2.08 g, 15.1 mmol, 2 eq) was added to a mixture of o-chlorocyclohexanone (1.00 g, 7.54 mmol, 1 eq) and p-methoxyphenol (1.12 g, 9.05 mmol, 1.2 eq) in toluene (12 mL). The reaction mixture was stirred at 90° C. for 1 h. The reaction was monitored by TLC (cyclohexane/ethyl acetate 8:2—stain:vanillin). Water (30 mL) and ethyl acetate (50 mL) were then added at room temperature and the aqueous layer was extracted with ethyl acetate (3×50 mL). The combined organic layer was then washed with 1N NaOH (4×30 mL), dried over sodium sulfate, filtered and concentrated. The crude brown oil was purified by flash chromatography (Macherey Nagel CHROMABOND® Flash RS 40 SiOH, cyclohexane/ethyl acetate 98:2 to 80:20) to afford intermediate compound 2 (1.08 g, 65%) as a white solid.

Mass (GC/MS): 220 [M]$^{+\bullet}$, 202, 174, 124, 109, 95, 81, 69, 55.

Synthesis of Intermediate Compound 3

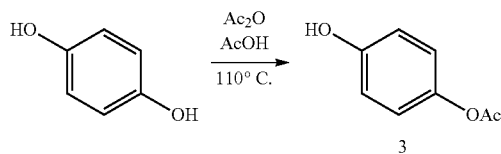 [SMILES: Oc1ccc(O)cc1 ; CC(=O)Oc1ccc(O)cc1]

Hydroquinone (1.00 g, 9.08 mmol, 1 eq) was dissolved in acetic acid (2.27 mL) and the solution was heated to 110° C. Acetic anhydride (0.425 mL, 4.54 mmol, 0.5 eq) was then added at this temperature and the mixture was stirred at 110° C. for 2 h. The mixture was then allowed to reach room temperature and acetic acid was removed by evaporation. Toluene (4.5 mL) was then added to the white solid and the suspension was filtered to remove the excess of hydroquinone. The filtrate was then concentrated to afford intermediate compound 3 (651 mg, 94%) as a yellowish oil.

Mass (GC/MS): 152 [M]$^{+\bullet}$, 143, 110, 81, 73, 55, 43.

Mass (GC/MS): 154 [M]$^{+\bullet}$, 124; 109; 93; 81; 65; 53.

Synthesis of Intermediate Compound 4

Synthesis of Intermediate Compound 6

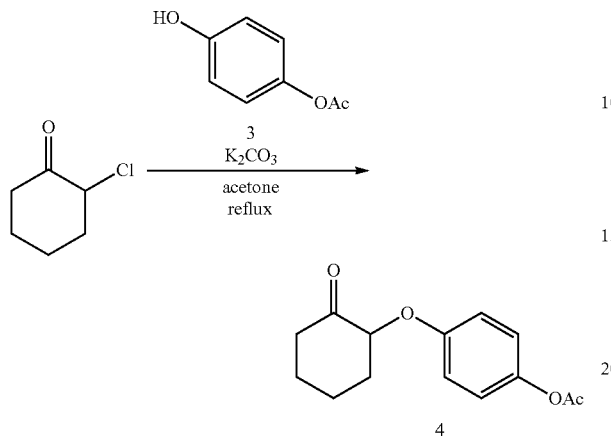

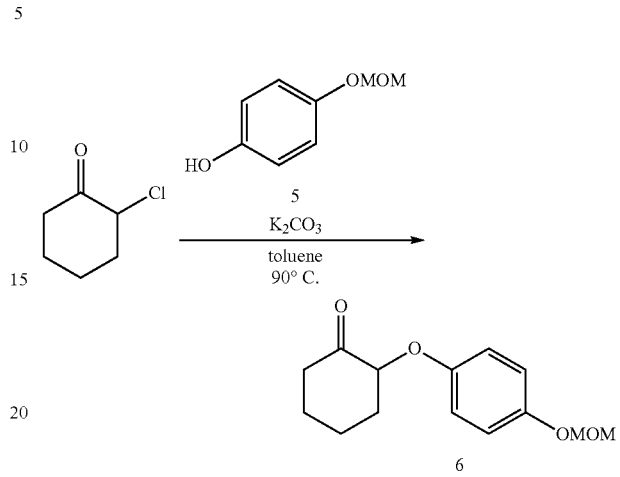

Under inert atmosphere, K$_2$CO$_3$ (0.21 g, 1.51 mmol, 2 eq) was added to a mixture of o-chlorocyclohexanone (0.100 g, 0.75 mmol, 1 eq) and intermediate compound 3 (0.172 g, 1.13 mmol, 1.5 eq) in acetone (1.5 mL). The reaction mixture was refluxed overnight. Water (5 mL) and diethyl ether (10 mL) were then added at room temperature and the aqueous layer was extracted with diethyl ether (3×20 mL). The combined organic layer was then washed with 1N NaOH (4×20 mL), dried over sodium sulfate, filtered and concentrated. The crude brown oil was purified by flash chromatography (Biotage® SNAP 10 g, cyclohexane/ethyl acetate 95:5 to 75:25) to afford intermediate compound 4 (29 mg, 15%) as a white solid.

Mass (GC/MS): 248 [M]$^{+\bullet}$, 206, 162, 110, 98, 91, 69, 55, 43.

Synthesis of Intermediate Compound 5

Under inert atmosphere intermediate compound 5 (1.0 g, 6.52 mmol, 1.2 eq.) followed by K$_2$CO$_3$ (1.50 g, 10.9 mmol, 2 eq) were added to a solution of 2-chlorocyclohexanone (720 mg; 5.43 mmol, 1 eq.) in dry toluene (11 mL). The mixture was heated at 90° C. for 1 h. At room temperature, water was added to the mixture, which was then extracted twice with ethyl acetate. The combined organic layer was washed twice with 1N NaOH, dried over sodium sulfate, filtered and concentrated to afford 1.02 g of crude oil. 720 mg of this crude material was purified by silica gel chromatography (Biotage® SNAP 50 g, cyclohexane/ethyl acetate 96:4 to 78:22) to afford intermediate compound 6 (582 mg, 61% extrapolated yield) as a colorless oil.

Mass (GC/MS): 250 [M]$^{+\bullet}$, 220; 154; 124; 110; 97; 81; 69; 55; 45.

Synthesis of Compound 7

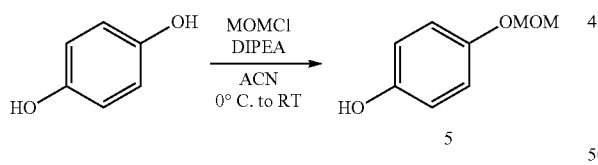

Hydroquinone (0.50 g, 4.54 mmol, 1 eq) was dissolved in acetonitrile (15 mL) under an inert atmosphere, and the solution was cooled to 0° C. MOMCl (517 µL, 6.81 mmol, 1.5 eq) followed by diisopropylethylamine (1.5 mL, 9.08 mmol, 2 eq) were successively added and the mixture was stirred overnight at room temperature. Methanol (200 µL) was added and the mixture was stirred at room temperature for 30 min. Acetonitrile was then removed under vacuum and 1M HCl (aq.) was added to the residue. The aqueous mixture was extracted twice with ethyl acetate and the combined organic extract was dried over sodium sulfate, filtered and concentrated to afford an orange oil (623 mg). This crude oil was purified by silica gel chromatography (Biotage® SNAP 50 g, cyclohexane/ethyl acetate 98:2 to 70:30) to afford intermediate compound 5 (228 mg, 33%) as a yellowish oil.

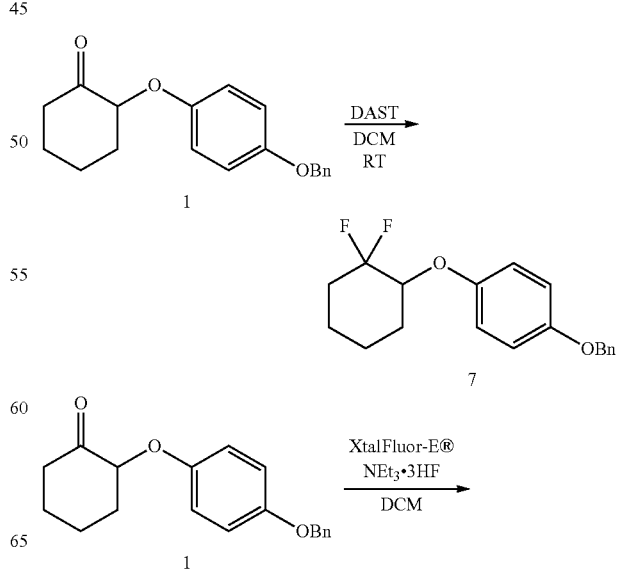

-continued

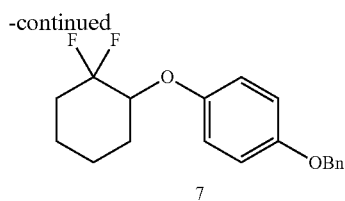

7

Route 1:

At room temperature, diethylaminosulfur trifluoride (3.33 mL, 27.3 mmol, 2.8 eq) was added to a solution of intermediate compound 1 (2.7 g, 9.11 mmol, 1 eq) in dry dichloromethane (55 mL) under inert atmosphere. The mixture was stirred overnight at room temperature before being poured on a mixture of ice and solid NaHCO$_3$. The cold mixture was stirred 15 min and dichloromethane was added. The aqueous layer was then extracted with dichloromethane (2×50 mL), dried over sodium sulfate, filtered and concentrated. The crude brown oil was purified on silica gel chromatography (Biotage® SNAP 100 g, cyclohexane/toluene 93:7 to 40:60) to afford compound 7 (1.87 g, 65%, 88% purity—$^{19}$F NMR) as colorless oil.

Route 2:

Under inert atmosphere, triethylamine trihydrofluoride (0.1 mL, 0.58 mmol, 2.8 eq.) was added at room temperature to a solution of XtalFluor-E® (135 mg, 0.59 mmol, 2.8 eq) in dry dichloromethane (0.5 mL). Intermediate compound 1 (61.3 mg, 0.207 mmol, 1 eq.) was then added and the reaction was stirred at the same temperature for 3 h. Dichloromethane was then added followed by sat. aq. NaHCO$_3$. The aqueous layer was extracted twice with dichloromethane and the combined organic layer was dried over sodium sulfate, filtered and concentrated. The crude material was purified by flash chromatography on silica gel (Biotage ZIP® 10, cyclohexane/toluene 98:2 to 50:50) to afford compound 7 (31 mg, 47%) as a colorless oil with an estimated purity ($^{19}$F NMR) of 98%.

$^{19}$F NMR (CDCl$_3$, 282.5 MHz): −105.3 (d, J=244 Hz, 1 F); −107.8 (brs, 1 F).

Mass (GC/MS): 318 [M]$^{+•}$, 55, 77, 91, 109, 227.

Synthesis of Compound 8

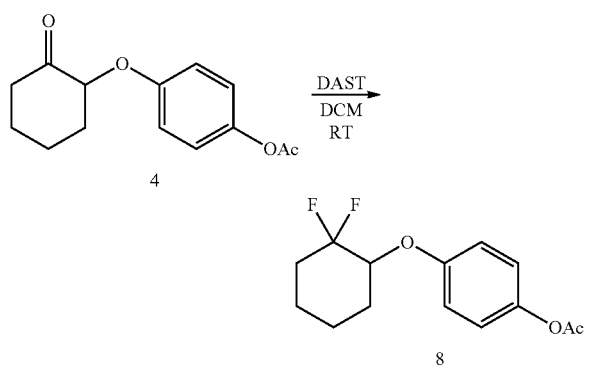

Diethylaminosulfur trifluoride (35 µL, 0.26 mmol, 2.7 eq) was added to a solution of intermediate compound 4 (24 mg, 0.1 mmol, 1 eq) in dry dichloromethane (537 µL) under inert atmosphere. The mixture was stirred overnight at room temperature before being poured on a mixture of ice and solid NaHCO$_3$. The cold mixture was stirred 15 min and dichloromethane was added. The aqueous layer was then extracted with dichloromethane (2×10 mL), dried over sodium sulfate, filtered and concentrated. The crude oil was purified on silica gel chromatography (Biotage® SNAP 10 g, cyclohexane/Et$_2$O 95:5 to 75:25) to afford compound 8 (16 mg, 61%, 84% purity-$^{19}$F NMR) as a colorless oil.

$^{19}$F NMR (CDCl$_3$, 282.5 MHz): −105.8 (d, J=243 Hz, 1 F); −107.8 (brs, 1 F).

Mass (GC/MS): 270 [M]$^{+•}$, 228, 110, 99, 77, 55, 43.

Synthesis of Compound 9

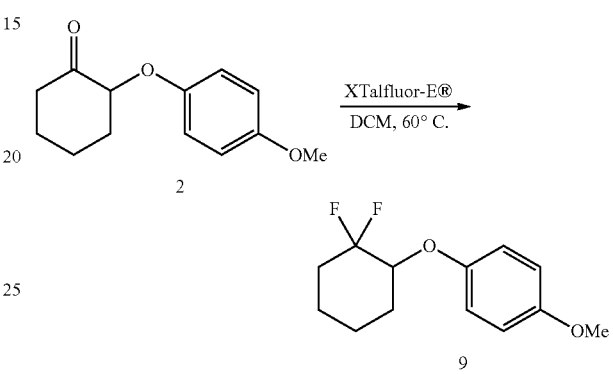

XtalFluor-E® (0.208 g, 0.91 mmol, 2 eq) was suspended in dry DCM (2 mL), under inert atmosphere. Triethylamine trihydrofluoride (110 µL, 0.68 mmol, 1.5 eq) was then added at room temperature followed by a solution of intermediate compound 2 (0.100 g, 0.45 mmol, 1 eq) in dry DCM (0.5 mL). The reaction was stirred under reflux for 2 h before being poured on a mixture of ice and solid NaHCO$_3$. The cold mixture was stirred 15 min and dichloromethane was added. The aqueous layer was then extracted with dichloromethane (2×10 mL) and the combined organic layer was washed with brine, dried over sodium sulfate, filtered and concentrated. The crude oil was purified on silica gel chromatography (Biotage® SNAP 10 g, cyclohexane/toluene 93:7 to 40:60) to afford compound 9 (58 mg, 53%, 98% purity—$^{19}$F NMR) as a yellowish oil.

$^{19}$F NMR (CDCl$_3$, 282.5 MHz): −105.3 (d, J=240 Hz, 1 F); −107.8 (brs, 1 F).

Mass (GC/MS): 242 [M]$^{+•}$, 221, 124, 109, 95, 73, 55.

Synthesis of Compound 10

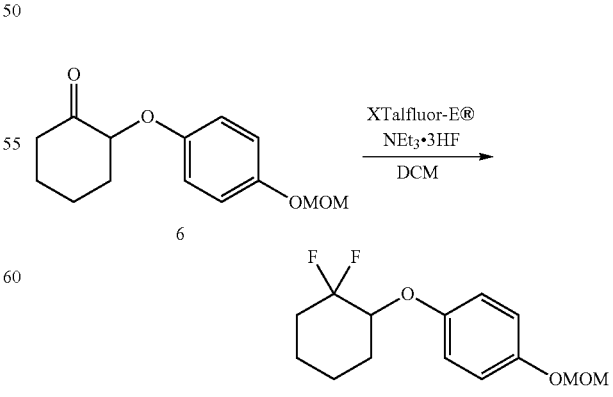

XtalFluor-E® (174 mg, 0.76 mmol, 3.8 eq) was suspended in dry DCM (0.4 mL), under inert atmosphere. Triethylamine trihydrofluoride (91 µL, 0.56 mmol, 2.8 eq) was then added at room temperature followed by a solution of intermediate compound 6 (50.0 mg, 0.20 mmol, 1 eq) in dry DCM (0.1 mL). The reaction was stirred at room temperature for 1 h30 before being poured on a saturated solution of NaHCO$_3$. The mixture was stirred 5 min and dichloromethane was added. The aqueous layer was then extracted with dichloromethane (2×) and the combined organic layer was dried over sodium sulfate, filtered and concentrated. The crude oil was purified on silica gel chromatography (Biotage® SNAP 10 g, cyclohexane/toluene 100:0 to 90:10) to afford 10 (27 mg, 50%, 93% purity—$^{19}$F NMR) as a colorless oil.

$^{19}$F NMR (CDCl$_3$, 282.5 MHz): −105.8 (brd, J=242 Hz, 1 F), −108.0 (brs, 1 F).

Mass (GC/MS): 272[M]$^{+\cdot}$, 242, 216, 124, 73.

Synthesis of Compound 11

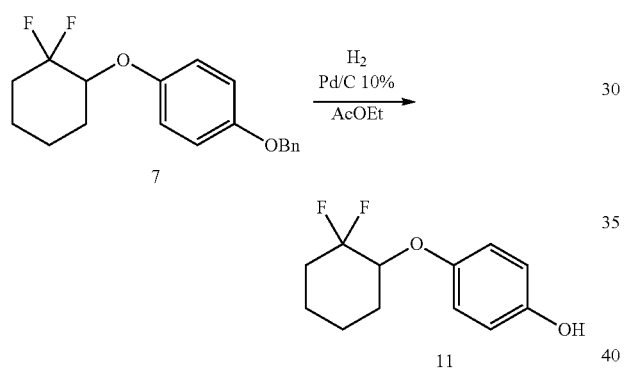

Pd/C 10% (6.42 g, 6.04 mmol, 0.1 eq) was added to a solution of compound 7 (19.2 g, 60.4 mmol, 1 eq) in ethyl acetate (275 mL). The mixture was stirred 16 h under hydrogen atmosphere at room temperature and was then filtered on millipore 0.45 µM and concentrated to afford a colorless oil (13.9 g) which was purified on silica gel chromatography (Biotage® SNAP 750 g, cyclohexane/diethyl ether 90:10 to 63:37 liquid injection) to afford compound 11 (9.8 g, 71%, racemate mixture) as an oil which slowly cristallizes in a white solid.

HPLC analysis: compound 11 was analysed using a ThermoFisher P1000XR HPLC system with an elution solvent ratio of 95:5 v/v heptane/isopropyl alcohol and a 4.6×250 mm, 5 µm Chiralpak® IA column, running 1 mL/min at 22° C. The detection system is a UV lamp at 225 nm. The enantiomers were eluted at tr=15.24 min and tr=16.80 min with relative amounts of 49.07% and 48.91% respectively.

$^{19}$F NMR (CDCl$_3$, 282.5 MHz): −105.7 (d, J=241 Hz, 1 F); −108.4 (brs, 1 F).

Mass (AP$^-$): 227.1 [M−H]$^-$.

Synthesis of Compound 12

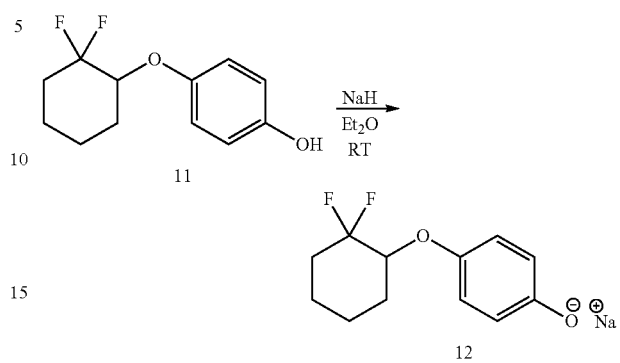

Sodium hydride (7.4 mg, 0.31 mmol, 1 eq) was added under inert atmosphere to a solution of compound 11 (70.0 mg, 0.31 mmol, 1 eq) in dry diethyl ether (0.7 mL). The reaction mixture was stirred overnight at room temperature. The resultant suspension was filtered, washed with diethyl ether and dried to afford compound 12 (43 mg, 61%) as white solid.

$^{19}$F NMR (MeOD, 282.5 MHz): −104.7 (d, J=244 Hz, 1 F); −108.6 (brs, 1 F).

Synthesis of Intermediate Compound 13

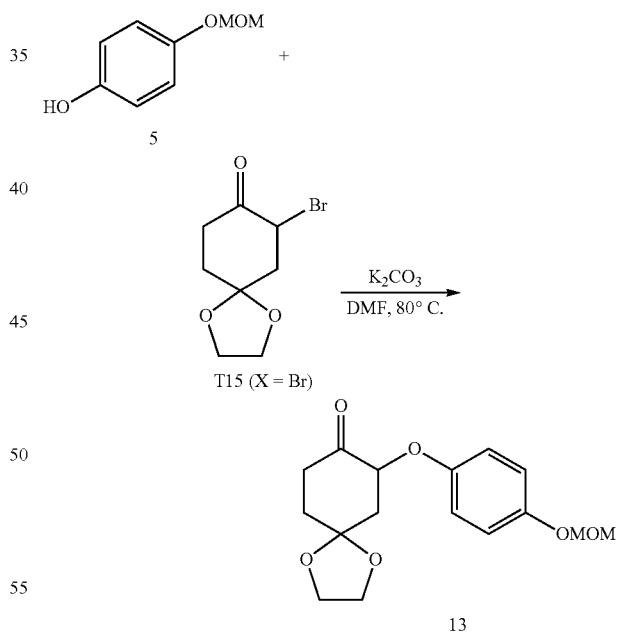

Under inert atmosphere, a solution of T15 (X=Br) (prepared as disclosed in *Chem. Eur. J.* 2007, 13, 3739-3756) (4.78 g, 20.3 mmol, 1.2 eq) in dry DMF (40 mL) was added to a solution of intermediate compound 5 (2.61 g, 16.9 mmol, 1 eq) and K$_2$CO$_3$ (2.34 g, 16.9 mmol, 1 eq) in dry DMF (16 mL) at room temperature. The reaction was then stirred at 80° C. for 5 h. The reaction was then allowed to reach room temperature and water was added followed by 1N NaOH. The mixture was then extracted with diethyl ether (3×) and the combined organic layer was washed with water, brine and was dried over sodium sulfate, filtered and concentrated to afford intermediate compound 13 (2.07 g, 40%) as a yellow solid. The crude intermediate compound 13 was engaged in the next step without further purification.

Mass (GC/MS): 308 [M]$^{+•}$, 278, 207, 155, 124, 111, 99, 86, 65, 55, 45.

Synthesis of compound 14

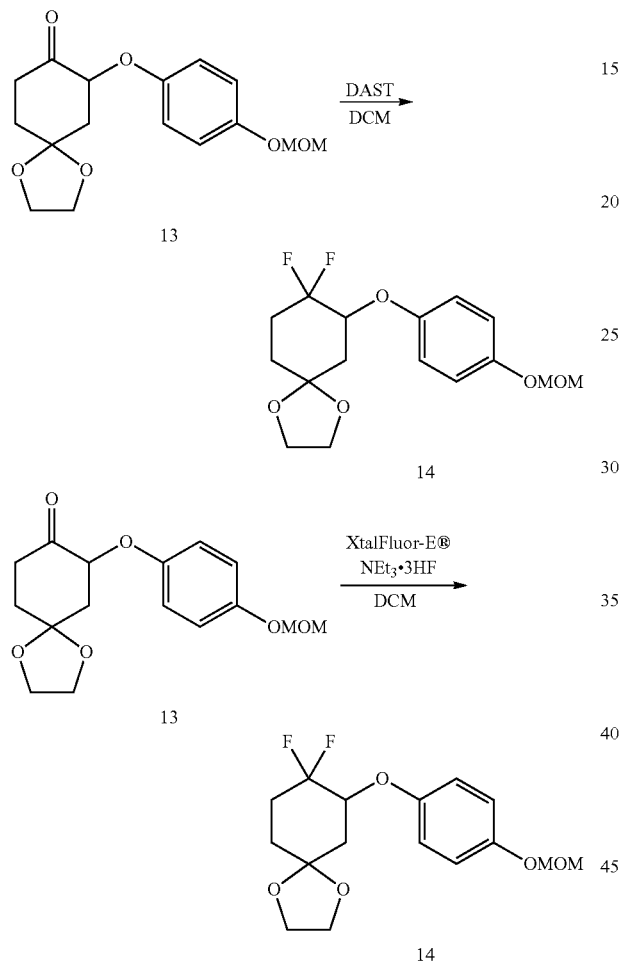

Route 1:

Under inert atmosphere, diethylaminosulfur trifluoride (79 μL, 0.59 mmol, 2.8 eq) was added dropwise to a solution of intermediate compound 13 (66.0 mg, 0.21 mmol, 1 eq) in dry dichloromethane (1.2 mL) and the reaction was stirred overnight at room temperature. The reaction mixture was then poured on a mixture of ice, water and solid NaHCO$_3$. The agitation was maintained 15 min and the aqueous layer was then extracted twice with dichloromethane. The combined organic layer was dried over sodium sulfate, filtered and concentrated. The crude material was purified by flash chromatography on silica gel (Biotage® SNAP 10 g, cyclohexane/ethyl acetate 97:3 to 72:28) to afford compound 14 (59 mg, 83%) with an estimated purity ($^{19}$F NMR) of 87%.

Route 2:

Under inert atmosphere, XtalFluor-E® (4.59 g, 20.0 mmol, 3 eq) and triethylamine trihydrofluoride (2.2 mL, 13.4 mmol, 2 eq.) were successively added at room temperature to a solution of intermediate compound 13 (2.06 g, 6.68 mmol, 1 eq.) in dry dichloromethane (13.4 mL). The reaction was stirred at the same temperature for 2 h. Dichloromethane was then added followed by sat. aq. NaHCO$_3$. The aqueous layer was extracted twice with dichloromethane and the combined organic layer was dried over sodium sulfate, filtered and concentrated. The crude material was purified by flash chromatography on silica gel (Biotage® SNAP 100 g, cyclohexane/ethyl acetate 98:2 to 75:25) to afford compound 14 (2.06 g, 76%) with an estimated purity ($^{19}$F NMR) of 95%.

$^{19}$F NMR (CDCl$_3$, 282.5 MHz): −107.8 (dm, J=238 Hz, 1 F); −120.9 (brd, J=236 Hz, 1 F).

Mass (GC/MS): 330 [M]$^{+•}$, 177, 157, 133, 113, 99, 85, 77, 65, 55, 45.

Synthesis of Compound 15

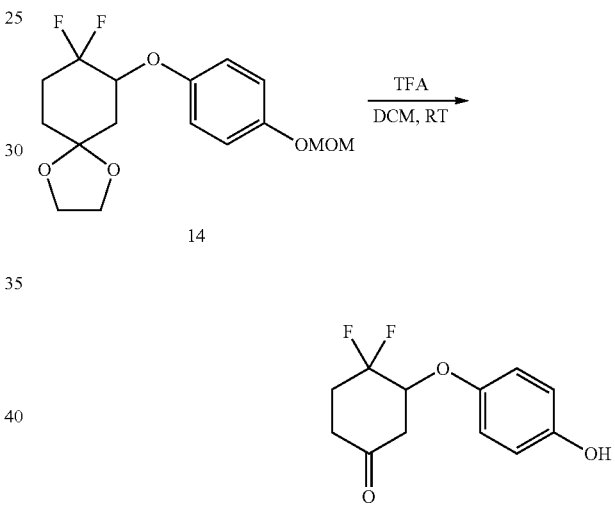

Under inert atmosphere, trifluoroacetic acid (8.1 mL, 109 mmol, 25 eq) was added at room temperature to a solution of compound 14 (1.44 g, 4.36 mmol, 1 eq) in dry dichloromethane (44 mL). The reaction was stirred overnight at room temperature. The mixture was diluted with dichloromethane and was poured onto sat. aq. NaHCO$_3$. The aqueous layer was extracted twice with dichloromethane and the combined organic layer was dried over sodium sulfate, filtered and concentrated. The crude material was purified by flash chromatography on silica gel (Biotage ZIP® 30 g, cyclohexane/ethyl acetate 98:2 to 60:40) to afford compound 15 (245 mg, 23%) as a white solid.

$^{19}$F NMR (CDCl$_3$, 282.5 MHz): −108.9 (dm, J=251 Hz, 1 F); −110.4 (dm, J=251 Hz, 1 F).

Mass (GC/MS): 242 [M]$^+$, 143, 133, 110, 104, 91, 85, 81, 77, 68, 63, 59, 55, 43.

Synthesis of Compound 16

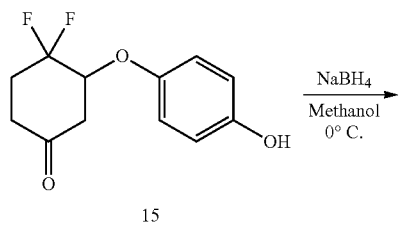

Under inert atmosphere, sodium borohydride (75.0 mg, 1.97 mmol, 2 eq) was added at 0° C. to a solution of compound 15 (239 mg, 0.99 mmol, 1 eq) in dry methanol (9.9 mL). The mixture was stirred at this temperature for 2 h. Sat. aq. NH$_4$Cl followed by brine were then added at 0° C. and the mixture was stirred for 15 min before being extracted twice with ethyl acetate. The combined organic layer was washed with water and brine, dried over sodium sulfate, filtered and concentrated. The crude material was purified by flash chromatography on silica gel (Biotage® SNAP 25 g, cyclohexane/ethyl acetate 90:10 to 65:35) to afford compound 16 (183 mg, 76%) as a white solid.

$^{19}$F NMR (MeOD, 282.5 MHz): −110.6 (dd, J=239 Hz, J=4 Hz, 1 F); −122.0 (brd, J=234 Hz, 1 F).

Mass (ESI-): 223.1 [M−HF−H]$^-$, 243.1 [M−H]$^-$, 285.1.

Synthesis of Compound 17

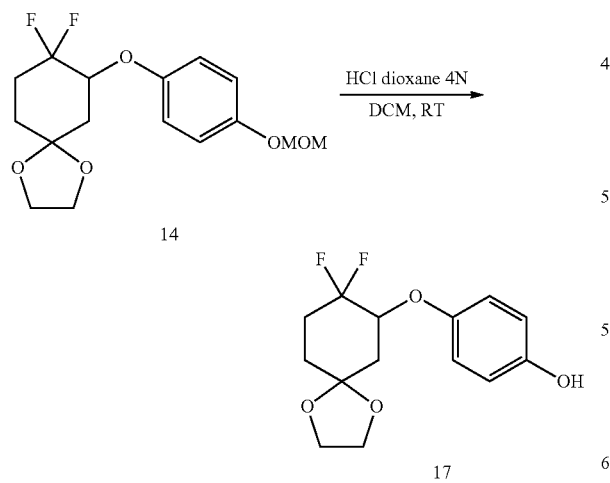

Under inert atmosphere, 4N HCl in dioxane (380 µL, 1.52 mmol, 10 eq) was added to a solution of compound 14 (50.0 mg, 0.15 mmol, 1 eq) in dry dichloromethane (1.5 mL). The mixture was stirred at room temperature for 4 h30 and at 40° C. overnight. The reaction was monitored by TLC (cyclohexane/ethyl acetate 6:4—stain: vanillin). An aliquot of the reaction was treated with sat. aq. NaHCO$_3$ and extracted with CDCl$_3$. The organic layer was filtered through Na$_2$SO$_4$ and analysed by $^{19}$F NMR. The analysis showed that the reaction was completed and that compound 17 was obtained with 61% conversion.

$^{19}$F-decoupled $^1$H NMR (CDCl$_3$, 282.5 MHz): −107.9 (d, J=255 Hz, 1 F); −120.9 (brd, J=240 Hz, 1 F).

Mass (GC/MS): 286 [M]$^{+\bullet}$, 221, 177, 110, 73, 85.

Synthesis of Intermediate Compound 18

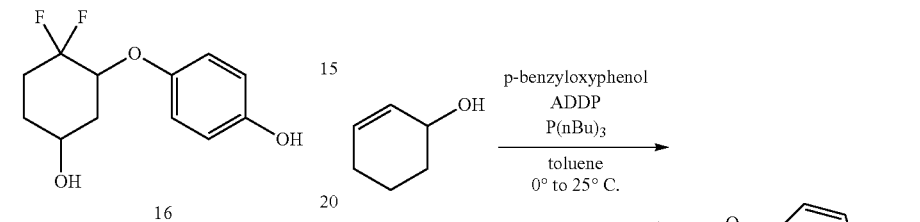

Benzyloxyphenol (245 mg, 1.2 mmol, 1.2 eq) and 1,1'-(azodicarbonyl)dipiperidine (303 mg, 1.2 mmol, 1.2 eq) were added under inert atmopshere to a solution of cyclohex-2-en-1-ol (0.1 mL, 1 mmol, 1 eq) in dry toluene (3.2 mL). The orange mixture was cooled to 0° C. and tri-n-butylphosphine (0.316 mL, 1.2 mmol, 1.2 eq) was added. The mixture was stirred at 25° C. for 5 min until the mixture jellified. Dichloromethane was added to the mixture, which was then concentrated to give the desired crude product as a white paste. The latter was purified by flash chromatography (Biotage® SNAP 25 g, cyclohexane/ethyl acetate 100:0 to 75:25) to afford intermediate compound 18 (40 mg, 92%) as a white solid.

Mass (GC/MS): 280 [M]$^{+\bullet}$, 200, 131, 91, 79, 65, 51, 44.

Synthesis of Intermediate Compound 19

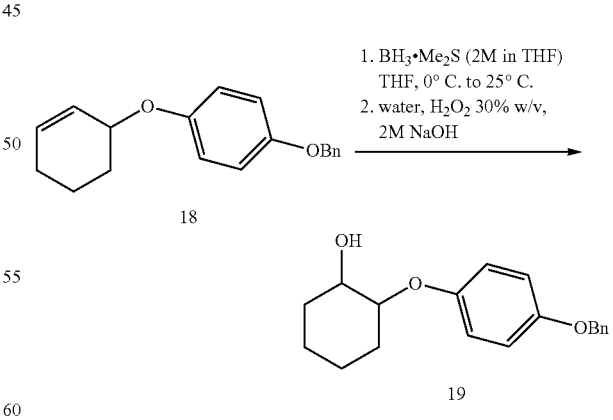

A solution of borane dimethyl sulfide complex (2M in THF, 2.27 mL, 4.55 mmol, 5 eq) was slowly added to a cold solution (0° C.) of intermediate compound 18 (255 mg, 0.91 mmol, 1 eq) in THF (4.6 mL) under an inert atmosphere. The mixture was stirred at 25° C. for 20 hours before being cooled to 0° C. Hydrogen peroxide 30% w/v (2.79 mL, 27.3 mmol, 30 eq), water (1.15 mL, 63.7 mmol, 70 eq) and 2M aq. NaOH (3.64 mL, 7.28 mmol, 8 eq) were then successively added. The mixture was stirred at 25° C. for an additional 3 h. Water was added to the mixture which was then extracted with ethyl acetate (3×30 mL). The organic layers were combined, dried over $Na_2SO_4$ and concentrated. The crude mixture was purified by flash chromatography (Biotage ZIP® 30 g, cyclohexane/ethyl acetate 100:0 to 35:65) to afford intermediate compound 19 (153 g, 56%) as a yellowish liquid which slowly crystallized.

Mass (API+): 321.1 $[M+Na]^+$.

2. Biological Activity of the Compounds According to the Invention

2.1. In Vitro Stability of Compound 11

The stability of compound 11 was evaluated by the released of hydroquinone, which is a potentially toxic compound, in different chemical conditions (extreme conditions, simulating the application of these molecules on the skin) and it was compared to the deoxyarbutin.

This study involved different tests as degradation test and chemical stability (various chemical solutions, pH and temperatures).

Methods

Preparation of Biological Solutions

Human Skin Solution

Eight pieces of skin of about 1 $cm^2$ were scratched and 7.2 mL of purified water were added. The solution was placed in ultrasonic bath.

Cell Extract (Fibroblasts or Keratinocytes)

The cultures of cells were performed in two steps.

In the first step, cells were pre-cultured: when the confluence was obtained, the culture medium was removed, replaced by trypsin in order to take off the cells, centrifuged and the sediment was taken back in suspension in a growing medium containing 10% of Fetal Bovine Serum. This cells suspension was divided into two flasks and put back in culture.

In the second step: when the confluence was obtained, the culture medium was removed, replaced by trypsin in order to take off the cells, centrifuged and the sediment was taken back in suspension in water. The cells in this suspension were counted and a solution containing $1 \cdot 10^5$ cells/mL was prepared. An extraction was performed using ultrasounds to lyse the cells in order to obtain a keratinocyte or fibroblast extract solution.

Analytical Method (HPLC-UV/DAD Method)

Column Atlantis dC18 150 mm*4.6 mm*3 µm Waters, 30° C. Injection 50 µl, 25° C. λ: 220 nm, 265 nm, 285 nm. A-Acetonitrile B-Water; 0.8 ml/min; elution gradient:

| Time (min) | % phase A | % phase B |
| --- | --- | --- |
| 0.0 | 20 | 80 |
| 5.0 | 25 | 75 |
| 6.0 | 90 | 10 |
| 9.0 | 90 | 10 |
| 9.5 | 20 | 80 |
| 12.0 | 20 | 80 | retention time 11=9.55 min; retention time Deoxyarbutin=9.19 min; retention time Hydroquinone=3.61 min.

This analytical method gave linear response for compound 11, Deoxyarbutin and Hydroquinone from 25 ng/mL to 1000 ng/mL. Dilution of samples had to be taken into account for each stability study to calculate the LLOQ of each compound.

Assay

The tested compounds are incubated in different solutions, at different times (see table 1). Then the analytical method was used to quantify remaining compounds and potential hydroquinone released (as possible degradation of compounds).

Hydroquinone (HQ) apparition is expressed as a percentage of initial compound 11 or Deoxyarbutin. The calculation was done in molar units and the limit of quantification fluctuates with the initial concentration.

$$\text{Percentage released } HQ = \frac{\text{Concentration } HQ}{\text{Concentration material}} \times 100$$

Results

TABLE 1

Mean percentage of Hydroquinone released from Deoxyarbutin or compound 11 in various conditions

| | | % Hydroquinone released | |
| --- | --- | --- | --- |
| Conditions | Time | From Deoxyarbutin | From 11 |
| Water at room temperature | 14 Days | 4.20 | 0.00 |
| Ringer's solution pH 5.5 at 70° C. | 24 H | 11.83 | 0.00 |
| Ringer's solution pH 8.5 at 70° C. | 24 H | 88.76 | 0.00 |
| Synthetic perspiration at RT | 48 H | 128.61 | 0.00 |

As shown in the table 1 above, hydroquinone was never released whatever the tested conditions from compound 11 unlike Deoxyarbutin.

2.2. In Vitro Efficacy of Compound 11 as Human Tyrosinase Inhibitor

The efficacy of compound 11 was evaluated by the inhibition of human tyrosinase in-tubo and compared to the deoxyarbutin and both α-arbutin and β-arbutin.

Methods

Preparation of Sample Solutions

Bis-Tris Buffer 100 mM pH=6.5 (Bis Tris free Base 2.09 g/Purified water up to 100 mL/HCl up to pH=6.5).

Substrate solution: L-DOPA (1 mg/mL) Solution B (L-DOPA 20 mg/Purified water up to 20 mL)

Enzyme solution: Tyrosinase (384.6 U/mL) Solution A (R-Human Like active Tyrosinase (5000 U/mL) 100 µL/Purified water 1200 µL)

Preparation of Test Solutions (for IC50 Test—Examples for Deoxyarbutin)

Inhibitors solutions deoxyarbutin (1 mg/mL): Deoxyarbutin 20 mg in purified water up to 20 mL

TABLE 2

Example of test solutions

|  | Test Deoxyarbutin 1 | Test Deoxyarbutin 2 | Test Deoxyarbutin 3 | Test Deoxyarbutin 4 | Positive control | Negative control |
|---|---|---|---|---|---|---|
| Solution B (substrate) (µL) | 25 | 25 | 25 | 25 | 25 | 25 |
| 95 µL of Deoxyarbutin solutions at (mg/mL) | 0.2 | 0.1 | 0.01 | 0.004 | 0 | 0.2 |
| Bis Tris buffer (µL) | 20 | 20 | 20 | 20 | 20 | 20 |
| Solution A (enz) (µL) | 20 | 20 | 20 | 20 | 20 | 0 |

Assay

This assay used a 96-well plate. Test solutions and controls were made several times. The absorbance (OD at 477 nm) was measured during all the experiment (kinetic), i.e. during 1 h, for each sample.

The kinetic profiles were determined for each concentration of enzyme inhibitors and the IC50 values, i.e. the concentration of inhibitor giving 50% of enzyme inhibition, were calculated and the results at time 20 min was used for the IC50 calculations.

In the conditions of the experiment the rate of conversion was stable between 5 and 30 minutes. The results were calculated from the OD measured at time point 20 min.

The determination of half maximal inhibitory concentration (IC50) was performed using the following formula.

$$\% \text{ inhibition} = 100 - \frac{OD_{sample\ T20min} \times 100}{OD_{positive\ control\ T20min}}$$

Results

Arbutins, Deoxyarbutin and compound 11 were tested as inhibitors of the human tyrosinase activity at different concentrations.

The IC50 values of both Deoxyarbutin and compound 11 were determined and compared in the following table 3. The IC50 values of both arbutins are reported in table 4.

TABLE 3

Calculated IC50 of Deoxyarbutin and compound 11

| Tyrosinase Concentration (300 U/mL) | Test #1 | Test #2 | Test #3 | Test #4 | Mean (mg/mL) | Molecular weight (g/mol) | IC50 (mM) |
|---|---|---|---|---|---|---|---|
| Compound 11 | 0.008 | 0.008 | 0.008 | 0.008 | 0.008 | 228.24 | 0.035 |
| Deoxyarbutin | 0.026 | 0.045 | 0.080 | 0.060 | 0.053 | 194.23 | 0.272 |

TABLE 4

Calculated IC50 of α-arbutin and β-arbutin

| Tyrosinase Concentration (170 U/mL) | Test #1 | Test #2 | Mean (mg/mL) | Molecular weight (g/mol) | IC50 (mM) |
|---|---|---|---|---|---|
| α-arbutin | 0.068 | 0.065 | 0.067 | 272.5 | 0.244 |
| β-arbutin | 0.116 | 0.132 | 0.124 | 272.5 | 0.454 |

The comparison of IC50 has shown that the compound 11 inhibits the human recombinant tyrosinase 7-8 times more than the Deoxyarbutin with IC50 of 0.035 mM and 0.272 mM respectively. Moreover compound 11 inhibits the human recombinant tyrosinase better than α-arbutin, and β-arbutin.

2.3. In Vitro Efficacy of Compound 16 as Human Tyrosinase Inhibitor

The efficacy of compound 16 was evaluated by the inhibition of human tyrosinase in tubo and compared to the compound 11.

Methods

The assay was performed with a ready-to-use kit from Feldan Inc (Canada): the HumanLike Tyrosinase Assay kit (ref A021-a-001Kit).

The protocol was performed as described in the instructions for use of the manufacturer. Briefly, this kit is intended for the determination of human tyrosinase activity in presence of different inhibitors. The kit measures the conversion of L-Tyrosine into a dopachrome complex absorbing at 490 nm. The time course of the assay is 20 minutes, after which the results are analyzed and compared.

Results

The compounds 11 and 16 have been tested at a final concentration of 1.12 mM.

The measured absorbances at 490 nm are reported in the table 5 and plotted in function of time in the FIG. 1.

TABLE 5 measured OD at 490 nm for 20 minutes with compound 11 and 16

| | | OD at 490 nm | | | |
|---|---|---|---|---|---|
| | | Negative control | Positive control | compound 11 1.12 mM | compound 16 1.12 mM |
| time (min) | 0 | 0.0000 | 0.0000 | 0.0000 | 0.0000 |
| | 1 | 0.0030 | 0.0100 | 0.0095 | 0.0105 |
| | 2 | 0.0060 | 0.0210 | 0.0190 | 0.0185 |
| | 3 | 0.0080 | 0.0320 | 0.0295 | 0.0285 |
| | 4 | 0.0110 | 0.0430 | 0.0400 | 0.0385 |
| | 5 | 0.0140 | 0.0550 | 0.0505 | 0.0505 |
| | 6 | 0.0180 | 0.0670 | 0.0610 | 0.0605 |

TABLE 5-continued measured OD at 490 nm for 20 minutes with compound 11 and 16

| | OD at 490 nm | | | |
|---|---|---|---|---|
| | Negative control | Positive control | compound 11 1.12 mM | compound 16 1.12 mM |
| 7 | 0.0210 | 0.0820 | 0.0715 | 0.0720 |
| 8 | 0.0230 | 0.0940 | 0.0825 | 0.0815 |
| 9 | 0.0270 | 0.1080 | 0.0925 | 0.0925 |
| 10 | 0.0310 | 0.1210 | 0.1035 | 0.1025 |
| 11 | 0.0350 | 0.1340 | 0.1135 | 0.1125 |
| 12 | 0.0390 | 0.1470 | 0.1245 | 0.1225 |
| 13 | 0.0430 | 0.1590 | 0.1355 | 0.1330 |
| 14 | 0.0460 | 0.1720 | 0.1465 | 0.1435 |
| 15 | 0.0500 | 0.1850 | 0.1575 | 0.1545 |
| 16 | 0.0550 | 0.1960 | 0.1685 | 0.1650 |
| 17 | 0.0580 | 0.2080 | 0.1790 | 0.1765 |
| 18 | 0.0630 | 0.2200 | 0.1900 | 0.1885 |
| 19 | 0.0660 | 0.2320 | 0.2010 | 0.2000 |
| 20 | 0.0700 | 0.2450 | 0.2120 | 0.2115 |

Moreover for each compound the efficacy as tyrosinase inhibitor was calculated using the following formula:

$$\text{Inhibitor efficacy} \frac{OD_{490nm} \text{ assay}}{OD_{490nm} \text{ positive control (no inhibitor)}} \times 100$$

The results are reported in the table 6.

TABLE 6

Inhibitor efficacy of compounds 11 and 16 at T = 20 min

| Compound at 1.12 mM | Inhibitor efficacy (%) |
|---|---|
| Compound 11 | 13.5 |
| Compound 16 | 13.7 |

In these tested conditions, compounds 16 and 11 have shown a similar efficacy as human tyrosinase inhibitor in vitro.

2.4. Evaluation of the Antioxidant Activity of Compound 11

The aim of the study was to evaluate the antioxidant activity of compound 11 by the spectrophotometric method of the free radical DPPH• (2,2-diphenyl-1-picrylhydrazyl). Indeed, antioxidants react with DPPH˙ (purple), a stable free radical which is reduced to DPPH-H (yellow), and in consequence, the absorbance is decreased from the DPPH˙ radical to the DPPH-H form. The degree of discoloration indicates the scavenging potential of the antioxidant compounds in terms of hydrogen donating ability (Popovici et al. Revue de génie industriel 2009, 4, 25-39).

The tested compounds were: Trolox ((±)-6-hydroxy-2,5,7,8-tetramethylchromane-2-carboxylic acid, Sigma Aldrich), as reference, and compound 11.
Methods
Preparation of Solutions A stock solution of DPPH• was prepared at 200 μmol/mL in methanol and diluted in methanol in order to have a final concentration of around 150 μmol/mL to obtain a DO close to 0.9 in a plate of 96 wells. The antioxidant stock solutions were prepared at 1 mg/mL in methanol and the tested solutions were prepared from these antioxidant stock solutions as described in Table 7 below.

TABLE 7

Four working solutions for each antioxidant tested were prepared in methanol at the following concentrations:

| | Concentration (mg/mL) | | | |
|---|---|---|---|---|
| Antioxidant | Solution 1 | Solution 2 | Solution 3 | Solution 4 |
| Trolox | 0.01 | 0.02 | 0.03 | 0.05 |
| Compound 11 | 0.05 | 0.10 | 0.15 | 0.2 |

Assay

50 μL of each solution of antioxidant was added to the wells. Then, 200 μL of DPPH˙ was added to each well.

The blank was prepared with only 250 μl of methanol and the negative control was prepared with 200 μL DPPH• and 50 μL of methanol.

The analysis was started immediately after the addition of DPPH• lasting for 2 hours (readings every 20 seconds). The absorbance was read at 515 nm. Each experiment was performed three times and had shown that the absorbance decreases while the concentration of antioxidant increased.
Results In order to evaluate the antioxidant activity of compound 11, the absorbance at the time T=30 min was selected for the further calculation of EC50.

TABLE 8

Measure of the absorbance (A) at 515 nm in the assays with compound 11

| | Compound 11 | | | | |
|---|---|---|---|---|---|
| | Solution 1 | Solution 2 | Solution 3 | Solution 4 | Negative control |
| A at 515 nm (T = 30 min) | 0.505 | 0.373 | 0.234 | 0.233 | — |
| $A_n$ at 515 nm (T = 30 min) | — | — | — | — | 0.71 |

The EC50 corresponds to the concentration of antioxidant necessary to reduce by 50% the activity of DPPH•. The activity of DPPH• is a percentage calculated as the ratio of $A/A_n \times 100\%$.

The EC50 is expressed as a molar ratio of antioxidant (compound 11)/DPPH• (Popovici et al. Revue de génie industriel 2009, 4, 25-39). The EC50 was determined from the graph representing the percentage of DPPH• in function of the above mentioned molar ratio (moles of compound 11/moles of DPPH•).

The antioxidant activity of compound 11 was compared to that of Trolox used as a reference (considered as 100%). The results are reported in table 9 below:

TABLE 9

Comparison of EC50 of compound 11 and Trolox

| Antioxidant | EC50 (Ratio antioxidant/DPPH•) Mean | Standard Deviation % |
|---|---|---|
| Trolox | 0.240 | 0.012 |
| Compound 11 | 0.772 | 0.009 |

The results in table 9 showed that compound 11 has an antioxidant activity, as a free radical scavenger activity, with an efficacy of 31.1% compared to that of Trolox.

2.5. In Vitro Human Skin Absorption of Compound 11

The aim of this study was to evaluate the absorption of compound 11 applied to excised human skin.

In vitro method using a Franz diffusion cell allows measuring the diffusion of chemicals into and across skin.

The tested compound is applied to the surface of a human skin explant separating the two chambers of a Franz diffusion cell. The compound remains on the skin for a specified time under specified conditions. The receptor fluid is sampled at time points throughout the experiment and analyzed for the tested compound. The skin may also be fractioned for separate analysis in epidermis or dermis layers.

Methods

The transcutaneous absorption was measured on human skin collected from the abdominoplasty of a single donor. At reception, the skin was defatted and cut in several fragments in order to perform Franz experiment. After that, it was frozen until use in Franz experiment.

The tested compounds were prepared at a defined concentration. After thawing, the skin was placed on the receptor side containing Ringer solution (6 mL).

The tested solutions were applied to the outer surface of the skin (exchange surface: 2 cm$^2$). The temperature was regulated at 35° C. in receptor side corresponding to a temperature of 32° C. at the surface of the skin during the experiment.

The tested compounds were quantified, at T0 h and T24 h in the receptor solution bathing the inner surface of the skin (determination of flux), or at T24 h in the fractionated skin extracts (epidermis or dermis).

To prepare the extracts, the skin explant is firstly divided in dermis and epidermis layers, then 500 µL of methanol were added on each piece of skin and incubated in an ultrasonic bath for 4 hours. 10 µl of this sample were collected, completed with 990 µl of methanol and vigorously shaken (vortex). Secondly the quantification of compounds by LC-MS/MS method was realized on 100 µl of the previous preparation added with 1000 µl of ultrapure water and 10 µl of an internal standard Conditions of LC-MS/MS Method Symmetri C18, 50 mm*2.1 mm, 3.5 µm, Waters, 40° C.

Gradient of elution: A-Purified water/B-Acetonitrile, flow 0.3 mL/min

| Time (min) | % phase A | % phase B |
|---|---|---|
| 0.0 | 90 | 10 |
| 2.0 | 90 | 10 |
| 2.1 | 0 | 100 |
| 7 | 0 | 100 |
| 7.1 | 90 | 10 |
| 9 | 90 | 10 |

| | Q1 Mass (amu) | Q3 Mass (amu) | Dwell (msec) | Parameters |
|---|---|---|---|---|
| Parameters of compound 11 | 227 | 108 | 150 | DP = −41; FP = −156; EP = −5; CE = −22; CXP = −18 |
| Parameters of deoxyarbutin | 193 | 108 | 150 | DP = −35; FP = −120; EP = −8; CE = −25; CXP = −5 |
| Internal standard: Pentylparaben | 207 | 136 | 150 | DP = −56; FP = −200; EP = −10; CE = −26; CXP = −11 |

Lower Limit of Quantification: 0.2 ng/ml for compound 11 and 0.5 ng/mL for deoxyarbutin Upper Limit of quantification: 100 ng/ml Assays and Results Quantification of Compound in the Receptor Fluid of Franz Cell 200 µl of compound 11 or deoxyarbutin, at a final concentration of 2 mg/ml (in water), were deposited on the skin explant.

Sampling: 500 µL from the receptor fluid were removed at T0 h (replaced by Ringer solution) and at T24 h. These samples were analyzed by LC-MS/MS method for quantification of compound 11 and deoxyarbutin (results not shown). The quantity measured allowed to calculate a flux and to compare the absorption profile across the skin of compound 11 and deoxyarbutin. The results are reported in table 10 below.

TABLE 10 skin absorption of compound 11 and deoxyarbutin

| Flux compound 11 (µg/h/cm$^2$) | | Flux deoxyarbutin (µg/h/cm$^2$) | |
|---|---|---|---|
| mean (n = 3) | sd | mean (n = 3) | sd |
| 2.71 | 0.63 | 3.98 | 0.37 |

These results showed that compound 11 is able to go through the skin and that its flux in these conditions is lower than that of deoxyarbutin. There is more risk of skin resorption (risk to reach the bloodstream) for deoxyarbutin.

Quantification of Compound in Skin Fractions

An emulsion of compound 11 was prepared at a final concentration of 0.1 mg/mL (in 90% purified water/5% ethanol/5% DMSO) and was deposited on the skin explant (200 µL).

The skin extracts were prepared at T24 h and the quantification of compound 11 was performed. The experiment was repeated 3 times.

The mean of compound 11 quantities measured for each fraction of dermis or epidermis is reported in the table 11 below.

TABLE 11 quantification of compound 11 in epidermis and dermis

| Skin extract | Compound 11 (µg/g of tissue) | Standard deviation (µg/g) |
|---|---|---|
| EPIDERMIS | 22.3 | 1.3 |
| DERMIS | 5.1 | 0.8 |

The results in table 11 showed that compound 11 is able to go into the different compartment of the skin and that the quantity measured in epidermis was drastically higher than the one measured in dermis. So compound 11 is able to reach the compartment of the skin where its activity is required (on melanocytes).

The invention claimed is:
1. A compound having the following formula (I):

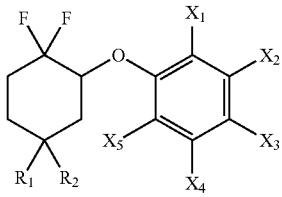

or a cosmetically or a pharmaceutically acceptable salt thereof, a stereoisomer or a mixture of stereoisomers in any proportion,
wherein:
$R_1$ and $R_2$ represent, independently from each other, a hydrogen atom or $OR_6$ or
$R_1$ and $R_2$ form together an oxo group (=O), or
$R_1$ and $R_2$ are linked together by a chain of formula —O(CH$_2$)$_n$O—, with n representing 2 or 3,
$X_1$, $X_2$, $X_4$, $X_5$ represent, independently from one another, a hydrogen atom or $OR_{16}$
$X_3$ represents a hydrogen atom, $OR_{16}$ or $OC(O)R_{17}$
with:
$R_6$ and $R_{16}$ representing, independently from one another, a hydrogen atom; or a ($C_1$-$C_6$)alkyl, ($C_2$-$C_6$)alkenyl, ($C_2$-$C_6$)alkynyl, ($C_3$-$C_7$)cycloalkyl, 5- to 7-membered heterocycloalkyl, aryl, heteroaryl, ($C_3$-$C_7$)cycloalkyl-($C_1$-$C_6$)alkyl, (5- to 7-membered heterocycloalkyl)-($C_1$-$C_6$)alkyl, aryl-($C_1$-$C_6$)alkyl or heteroaryl-($C_1$-$C_6$)alkyl group, said group being optionally substituted by one or several groups selected from a halogen atom, a ($C_1$-$C_6$)alkyl group and a ($C_1$-$C_6$)alkoxy group, and
$R_{17}$ representing a ($C_1$-$C_6$)alkyl, ($C_2$-$C_6$)alkenyl, ($C_2$-$C_6$)alkynyl, ($C_3$-$C_7$)cycloalkyl, 5- to 7-membered heterocycloalkyl, aryl, heteroaryl, ($C_3$-$C_7$)cycloalkyl-($C_1$-$C_6$)alkyl, (5- to 7-membered heterocycloalkyl)-($C_1$-$C_6$)alkyl, aryl-($C_1$-$C_6$)alkyl or heteroaryl-($C_1$-$C_6$)alkyl group, said group being optionally substituted by one or several groups selected from a halogen atom, a ($C_1$-$C_6$)alkyl group and a ($C_1$-$C_6$)alkoxy group,
wherein an aryl is an aromatic hydrocarbon group comprising 6 to 10 carbon atoms and comprising one or more fused rings;
wherein a heteroaryl is an aromatic group, having 5 to 10 members comprising one or more fused rings, in which the atoms of the ring(s) consist of one or more heteroatoms selected from nitrogen, oxygen and sulphur atoms, the remainder being carbon atoms;
wherein a 5- to 7-membered heterocycloalkyl is a saturated hydrocarbon cycle having 5 to 7 members and in which one or several carbon atoms are each replaced with a nitrogen, oxygen or sulphur atom.
2. The compound according to claim 1, wherein $X_1$, $X_2$, $X_4$ and $X_5$ each represents a hydrogen atom and $X_3$ does not represent a hydrogen atom.
3. The compound according to claim 1, wherein:
$R_6$ and $R_{16}$ represent, independently from one another, a hydrogen atom; or a ($C_1$-$C_6$)alkyl, aryl, or aryl-($C_1$-$C_6$)alkyl group being optionally substituted by one or several groups selected from a halogen atom, a ($C_1$-$C_6$)alkyl group and a ($C_1$-$C_6$)alkoxy group, and $R_{17}$ represents a ($C_1$-$C_6$)alkyl, aryl, or aryl-($C_1$-$C_6$)alkyl group, said group being optionally substituted by one or several groups selected from a halogen atom, a ($C_1$-$C_6$)alkyl group and a ($C_1$-$C_6$)alkoxy group.
4. The compound according to claim 1, wherein it is chosen from the following compounds:

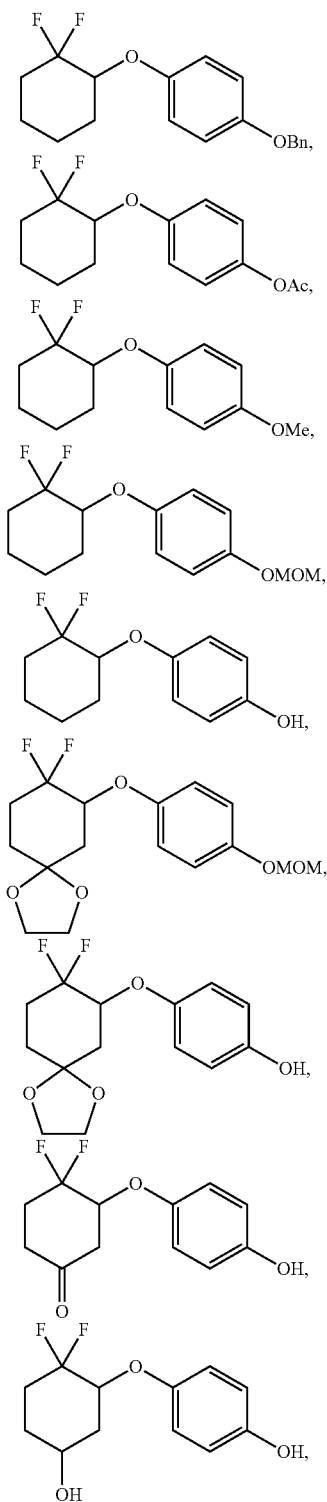

and cosmetically and pharmaceutically salts thereof.

5. A cosmetic or pharmaceutical composition comprising at least one compound of formula (I) as defined in claim 1 and at least one cosmetically or pharmaceutically acceptable excipient.

6. The compound according to claim 3, wherein:

$R_6$ and $R_{16}$ represent, independently from one another, a hydrogen atom; or a $(C_1$-$C_6)$alkyl, aryl, or aryl-$(C_1$-$C_6)$alkyl group, said group being optionally substituted by one or several groups selected from a $(C_1$-$C_6)$alkyl group and a $(C_1$-$C_6)$alkoxy group, and $R_{17}$ represents a $(C_1$-$C_6)$alkyl, aryl, or aryl-$(C_1$-$C_6)$alkyl group, said group being optionally substituted by one or several groups selected from a $(C_1$-$C_6)$alkyl group and a $(C_1$-$C_6)$alkoxy group.

7. A method for depigmenting, lightening, bleaching or whitening a skin comprising applying on said skin an efficient amount of a compound of formula (I) according to claim 1.

8. A method for treating a pigmentation disorder comprising applying on a skin of a person in need thereof an efficient amount of a compound of formula (I) according to claim 1.

9. The method according to claim 8, wherein the pigmentation disorder is a hyperpigmentation.

10. The method according to claim 9, wherein the hyperpigmentation is lentigo, melasma, ephelides, postinflammatory hyperpigmentation, or a hyperpigmentation caused by drugs, chemicals or sun.

11. A method for inhibiting or reducing oxidative stress comprising administering to a person in need thereof an efficient amount of a compound of formula (I) according to claim 1.

12. The method according to claim 11, wherein the reducing oxidative stress is due to UV.

13. The method according to claim 11, wherein the administrating is performed via a topical administration on the skin.

* * * * *